(12) United States Patent
Joko et al.

(10) Patent No.: US 8,137,265 B2
(45) Date of Patent: Mar. 20, 2012

(54) ENDOSCOPE, ENDOSCOPE SYSTEM, AND SWITCHING CIRCUIT MEMBER FOR ENDOSCOPE

(75) Inventors: Hidehiro Joko, Hachioji (JP); Takayuki Hanawa, Hachioji (JP)

(73) Assignee: Olympus Medical Systems Corp. (JP)

( * ) Notice: Subject to any disclaimer, the term of this patent is extended or adjusted under 35 U.S.C. 154(b) by 1218 days.

(21) Appl. No.: 11/817,368

(22) PCT Filed: Feb. 24, 2006

(86) PCT No.: PCT/JP2006/303408
§ 371 (c)(1),
(2), (4) Date: Aug. 29, 2007

(87) PCT Pub. No.: WO2006/100871
PCT Pub. Date: Sep. 28, 2006

(65) Prior Publication Data
US 2009/0082624 A1 Mar. 26, 2009

(30) Foreign Application Priority Data

Mar. 18, 2005 (JP) .................. 2005-080363
Mar. 18, 2005 (JP) .................. 2005-080364

(51) Int. Cl.
*A61B 1/00* (2006.01)
*A61B 1/04* (2006.01)
(52) U.S. Cl. .................................................. 600/118
(58) Field of Classification Search .............. 600/113, 600/118, 109, 160; 348/72, 74, 75, 76
See application file for complete search history.

(56) References Cited

U.S. PATENT DOCUMENTS

| 4,601,284 | A | * | 7/1986 | Arakawa et al. | 600/112 |
| 4,901,039 | A | * | 2/1990 | Corzine et al. | 333/1 |
| 5,178,130 | A | * | 1/1993 | Kaiya | 600/109 |
| 5,196,928 | A | * | 3/1993 | Karasawa et al. | 348/65 |
| 5,547,455 | A | * | 8/1996 | McKenna et al. | 600/113 |
| 6,217,510 | B1 | | 4/2001 | Ozawa et al. | |

(Continued)

FOREIGN PATENT DOCUMENTS

EP 1 637 062 A1 6/2004

(Continued)

OTHER PUBLICATIONS

Japanese Office Action dated Dec. 22, 2009 in corresponding Japanese Patent Application No. 2005-080363 (with English language translation).

(Continued)

*Primary Examiner* — Philip R Smith
*Assistant Examiner* — William Chou
(74) *Attorney, Agent, or Firm* — Ostrolenk Faber LLP

(57) ABSTRACT

The present invention relates to an endoscope to perform observation using a plurality of image pick up units and an endoscope system including such an endoscope, and its object is to provide an endoscope and an endoscope system having a simplified structure and a reduced cost. There is provided an endoscope including a plurality of image pick up units (24a, 24b) to pick up an observation image, a connector (28) to be connected with an external device (46) to perform signal processing, and a switching circuit portion (26) electrically connected with each image pick up unit (24a, 24b) and the connector (28) and configured to switch the plurality of image pick up units (24a, 24b) so that one of the image pick up units (24a, 24b) transmits/receives a signal to/from the connector (28).

5 Claims, 15 Drawing Sheets

U.S. PATENT DOCUMENTS

| | | | |
|---|---|---|---|
| 2001/0052930 A1* | 12/2001 | Adair et al. | 348/65 |
| 2003/0122926 A1* | 7/2003 | Kumei et al. | 348/65 |
| 2003/0133011 A1 | 7/2003 | Amling et al. | |
| 2004/0171912 A1 | 9/2004 | Shimizu | |
| 2004/0215060 A1 | 10/2004 | Ueno et al. | |
| 2006/0161047 A1* | 7/2006 | Miyoshi | 600/157 |
| 2006/0184023 A1* | 8/2006 | Satoh | 600/437 |
| 2006/0224040 A1* | 10/2006 | Khait et al. | 600/102 |
| 2006/0235273 A1* | 10/2006 | Moriyama et al. | 600/113 |

FOREIGN PATENT DOCUMENTS

| | | |
|---|---|---|
| EP | 1 665 978 A1 | 9/2004 |
| JP | 61-260213 | 11/1986 |
| JP | 1-138854 | 5/1989 |
| JP | 2-122772 | 5/1990 |
| JP | 6-154155 | 6/1994 |
| JP | 6-178757 | 6/1994 |
| JP | 8-140929 | 6/1996 |
| JP | 10-179516 | 7/1998 |
| JP | 11-113839 | 4/1999 |
| JP | 11-344678 | 12/1999 |
| JP | 2003-174997 | 6/2003 |
| JP | 2005-95467 | 4/2005 |
| WO | WO 98/14927 | 4/1998 |
| WO | WO 2004/112591 | 12/2004 |
| WO | WO 2005/027738 A1 | 3/2005 |

OTHER PUBLICATIONS

Chinese Office Action mailed Jun. 26, 2009 in corresponding Chinese Patent Application No. 200680003948.6 (with English language translation).

PCT International Search Report and Written Opinion dated Apr. 25, 2006 issued in corresponding PCT Application No. PCT/JP2066/303408.

Search Report issued by European Patent Office in connection with corresponding application No. EP 06 71 4547 on Oct. 5, 2010.

Japanese Office Action mailed Sep. 29, 2009 in corresponding Japanese Patent Application No. 2005-080363 (with English language translation).

Japanese Office Action mailed Sep. 29, 2009 in corresponding Japanese Patent Application No. 2005-080364 (with English language translation).

* cited by examiner

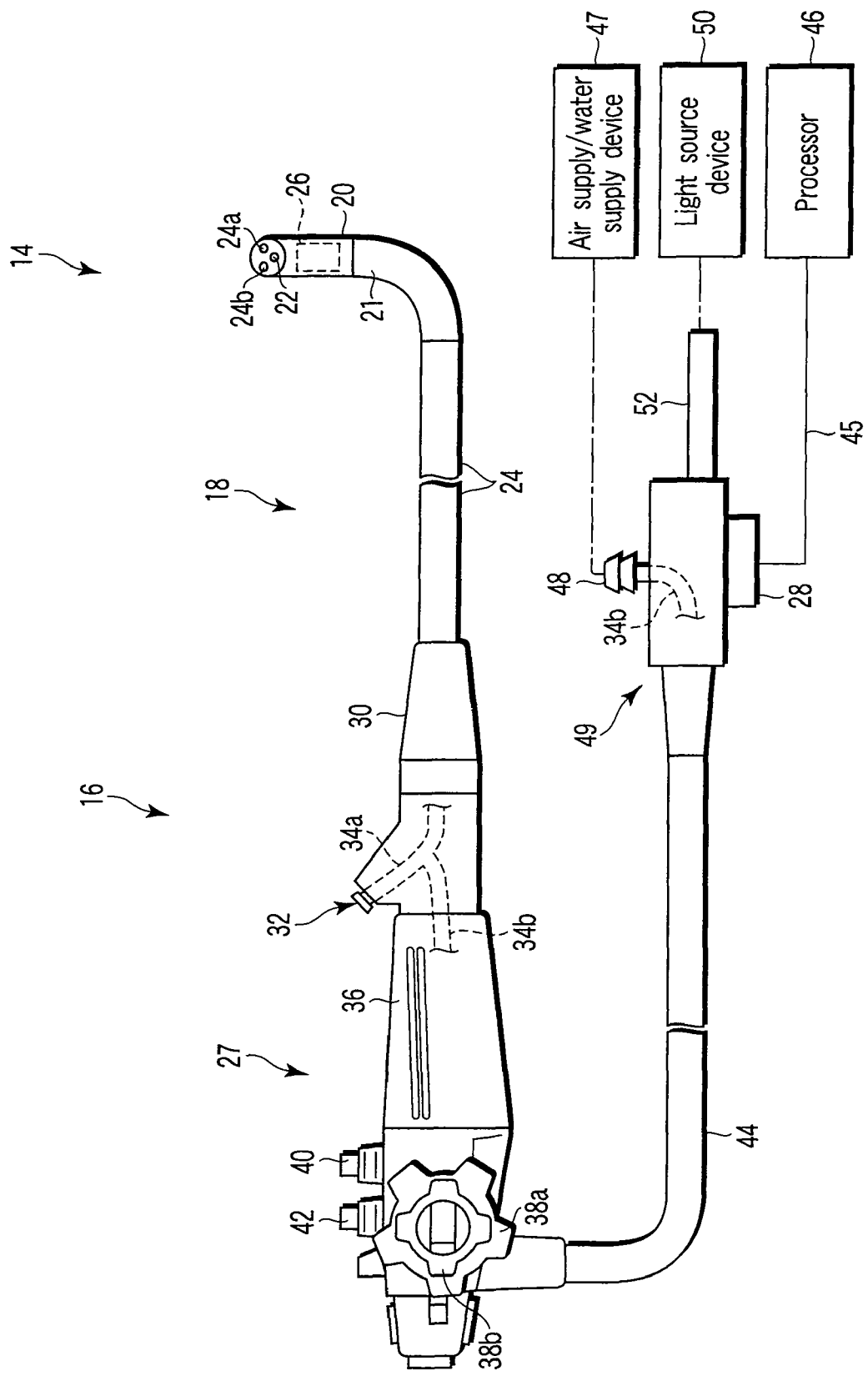
F I G. 1

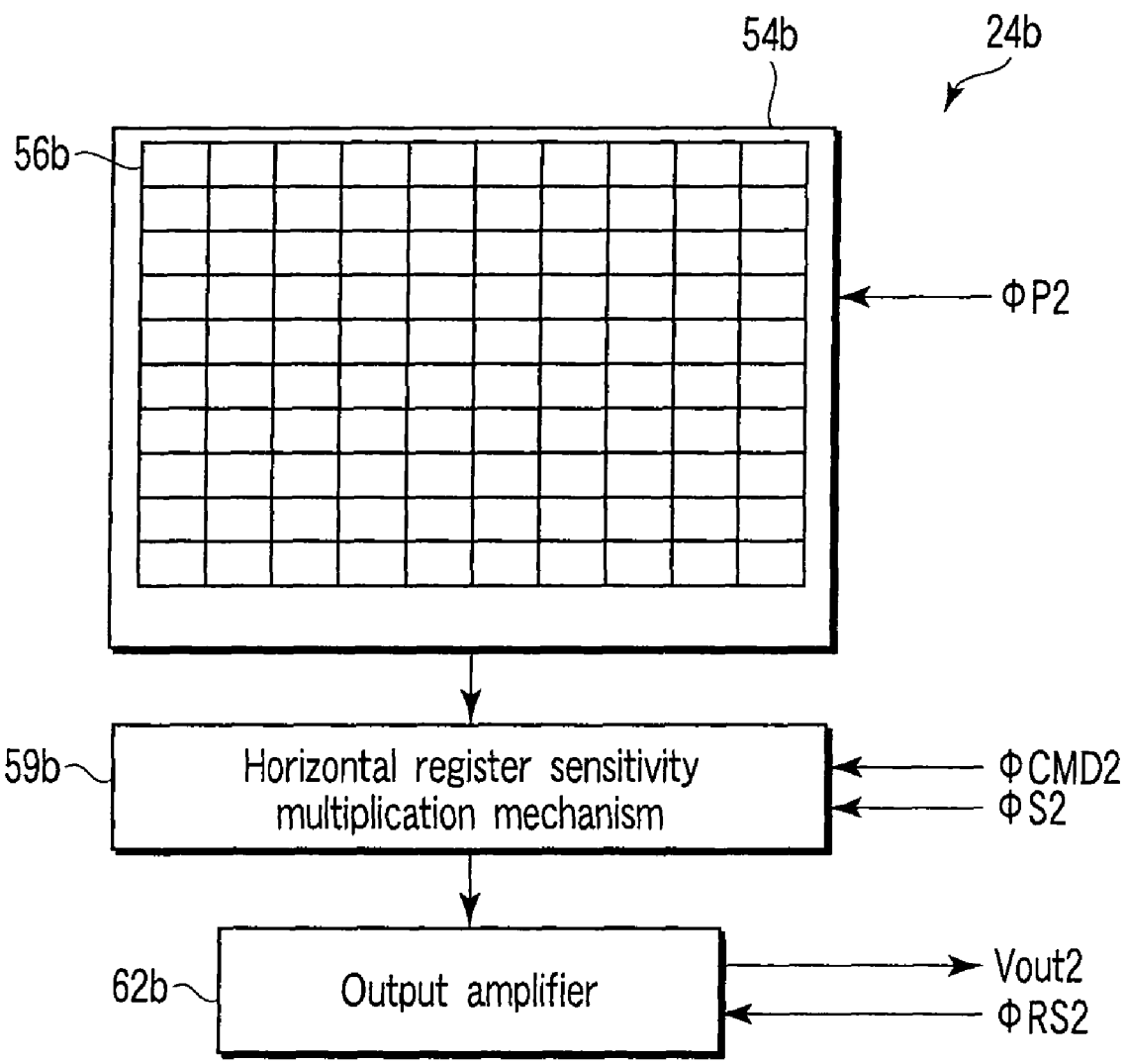
F I G. 2B

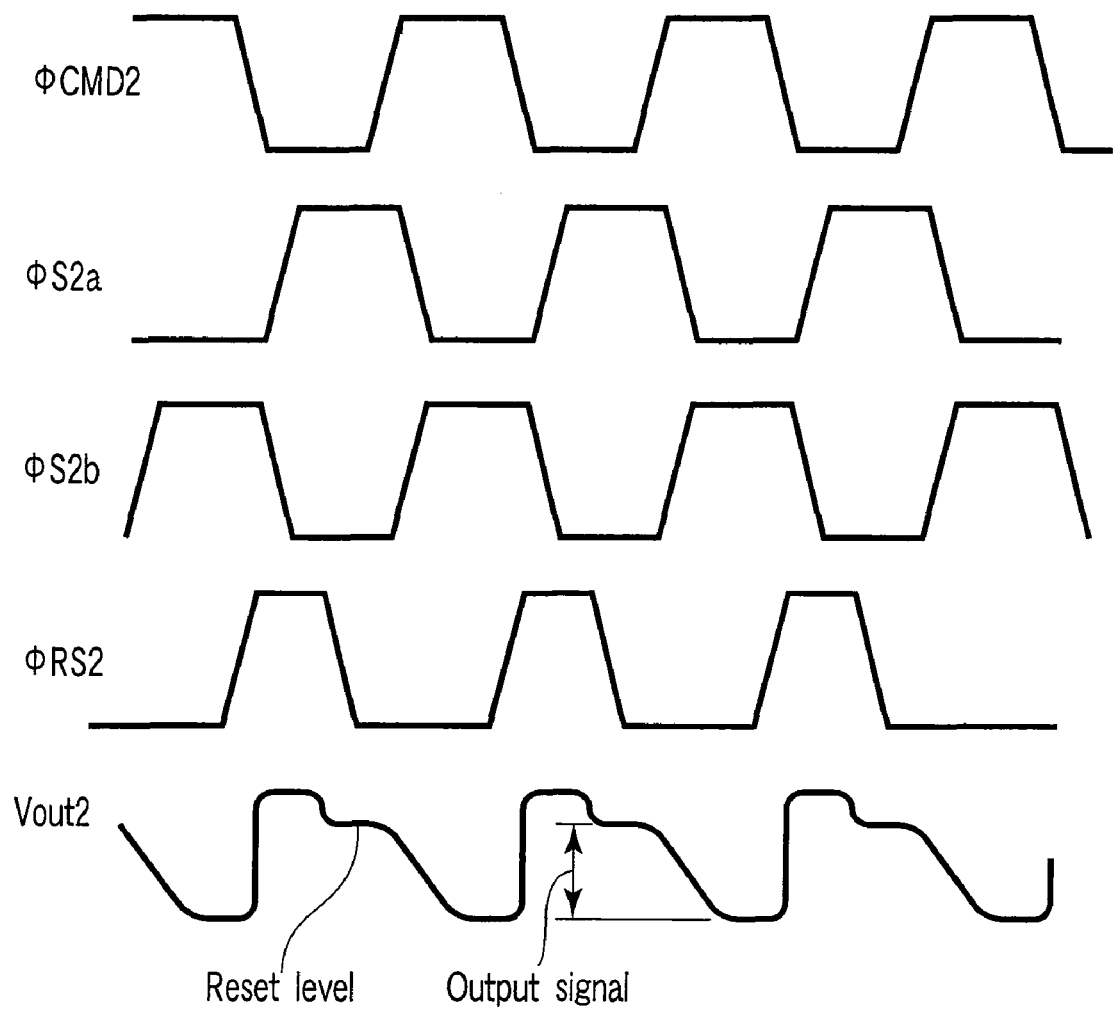
F I G. 2C

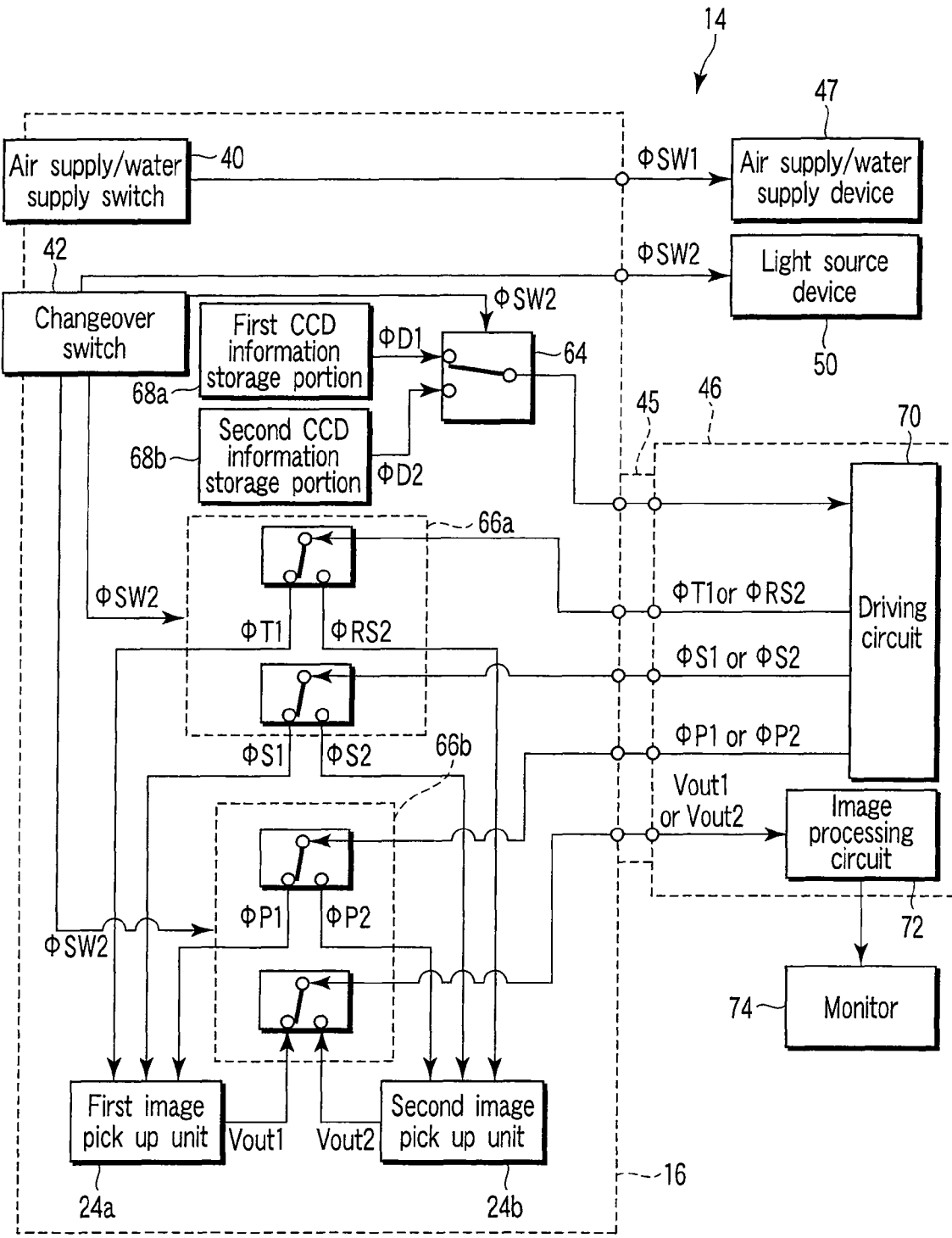
F I G. 3

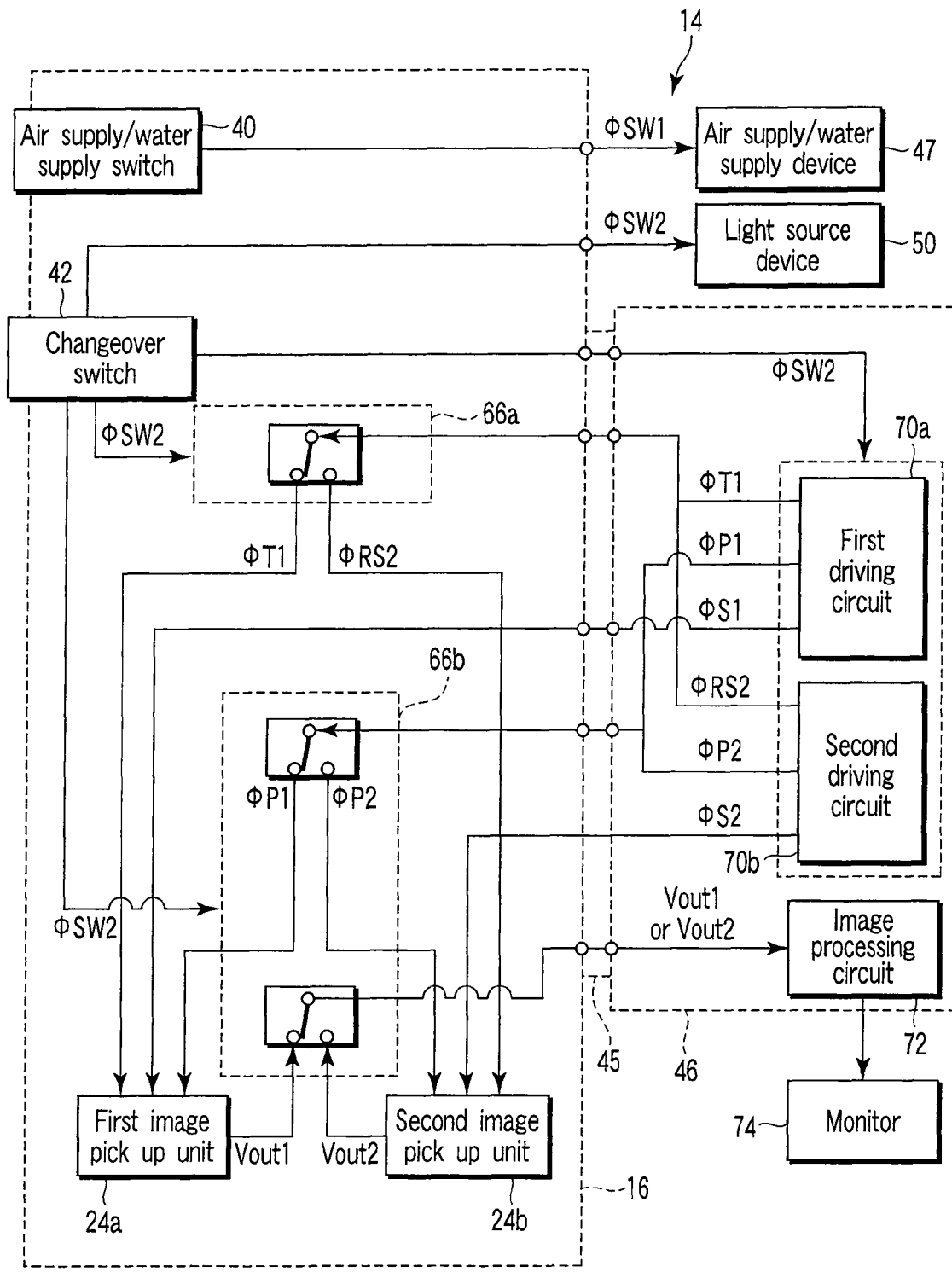
F I G. 11

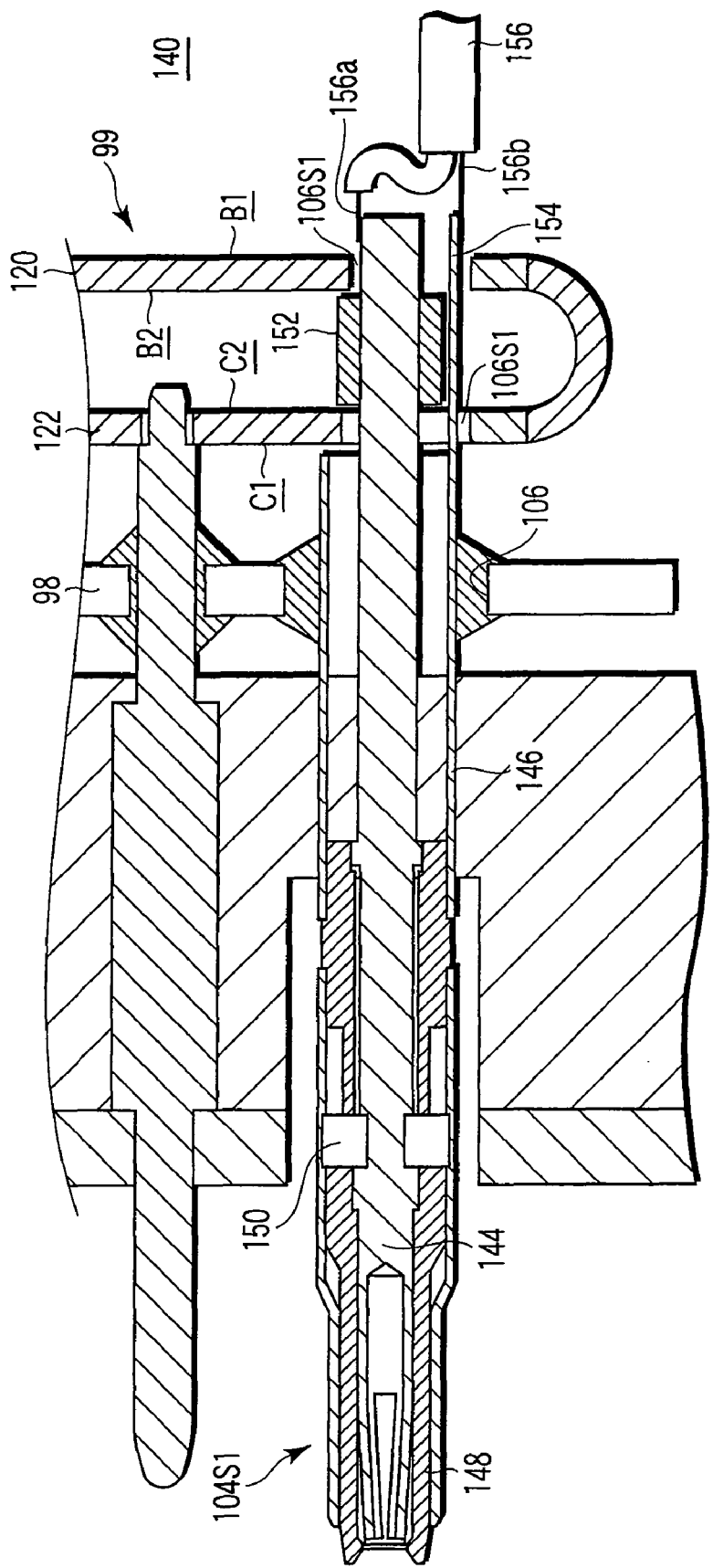
F I G. 12

ENDOSCOPE, ENDOSCOPE SYSTEM, AND SWITCHING CIRCUIT MEMBER FOR ENDOSCOPE

TECHNICAL FIELD

The present invention relates to an endoscope to perform observation using a plurality of image pick up units, and an endoscope system including such an endoscope.

BACKGROUND ART

An endoscope has been conventionally used, whose elongated insertion portion is inserted into a body cavity to observe the inside of the body cavity. In such an endoscope, an image pick up unit to obtain an observation image is arranged at a distal end of the insertion portion. A plurality of image pick up units which are of different types may be used to obtain an appropriate image meeting an observation purpose.

For example, in an endoscope disclosed in Jpn. Pat. Appln. KOKAI Publication No. 6-154155, first and second image pick up units having different angles of view are used.

In more detail, the endoscope disclosed in Jpn. Pat. Appln. KOKAI Publication No. 6-154155 includes an elongated insertion portion to be inserted into a body cavity, and an operating portion to be operated by an operator is arranged at a proximal end of the insertion portion. A universal cable extends from the operating portion, and a connector portion to connect the endoscope with an external device is arranged at an extending end of the universal cable.

First and second signal lines extends from the first and second image pick up units arranged at the distal end of the insertion portion, and the first and second signal lines are respectively inserted through the insertion portion, the operating portion, and the universal cable, and then connected with first and second connectors in the connector portion. The first and second connectors are respectively connected with first and second video processors to perform signal processing, through first and second scope cables.

The first and second video processors respectively output driving signals to the first and second image pick up units to drive the first and second image pick up units, process image signals input from the first and second image pick up units, and output the processed signals to a changeover switch portion.

The changeover switch portion selects one of the image signals from the first and second video processors, and outputs the selected signal to a monitor to selectively display one of images obtained by the first image pick up unit and the second image pick up unit on the monitor. For example, the image pick up unit with a narrow viewing angle is used to facilitate observation of an insertion target when inserting the endoscope, and the image pick up unit with a wide viewing angle is used to facilitate observation of a peripheral section when removing the endoscope.

DISCLOSURE OF INVENTION

In the endoscope disclosed in Jpn. Pat. Appln. KOKAI Publication No. 6-154155, the plurality of signal lines are extended over the substantially entire length of the endoscope and the plurality of connectors must be arranged in the connector portion in order to selectively display images obtained by the plurality of image pick up units, resulting in a complicated structure of the endoscope.

Further, when the endoscope disclosed in Jpn. Pat. Appln. KOKAI Publication No. 6-154155 is used to form an endoscope system that selectively displays one of images obtained by the first image pick up unit and the second image pick up unit, a plurality of scope cables and a plurality of video processors are required, thereby complicating the endoscope system.

In view of the above-explained problems, it is an object of the present invention to provide an endoscope and an endoscope system having a simplified structure and a reduced cost.

In an aspect of the present invention, an endoscope is characterized by including: a plurality of image pick up units to pick up an observation image; a connector to be connected with an external device to perform signal processing; and a switching circuit portion electrically connected with the respective image pick up units and the connector and configured to switch the plurality of image pick up units so that one of the image pick up units transmits/receives a signal to/from the connector.

In the endoscope, the signal is transmitted/received between one image pick up unit and the external device to obtain the observation image by the one image pick up unit, the image pick up unit that transmits/receives the signal to/from the external device is switched from the one image pick up unit to another image pick up unit by the switching circuit portion, and the signal is transmitted/received between another image pick up unit and the external device to obtain the observation image by the another image pick up unit.

In a preferred aspect of the present invention, the endoscope is characterized by further including a changeover switch to operate the switching circuit portion.

In the endoscope, the changeover switch in the endoscope is operated to perform the switching of the image pick up units.

In another aspect of the present invention, an endoscope characterized by including: an insertion portion to be inserted into a body cavity with a distal end thereof forward; an operating portion provided at a proximal end of the insertion portion; a cable extending from the operating portion; a plurality of image pick up units provided at the distal end of the insertion portion and to pick up an observation image; a connector provided at an extended end of the cable and to be connected with an external device to perform signal processing; and a switching circuit portion electrically connected with the respective image pick up units and the connector and configured to switch the plurality of image pick up units so that one of the image pick up units transmits/receives a signal to/from the connector.

In the endoscope, the insertion portion is inserted into the body cavity, the signal is transmitted/received between one image pick up unit at the distal end of the insertion portion and the external device to obtain the observation image of the inside of the body cavity by the one image pick up unit, the image pick up unit that transmits/receives the signal to/from the external device is switched from the one image pick up unit to another image pick up unit at the distal end of the insertion portion by the switching circuit portion, and the signal is transmitted/received between another image pick up unit and the external device to obtain the observation image of the inside of the body cavity by the another image pick up unit.

In a preferred aspect of the present invention, the endoscope is characterized in that the operating portion includes a changeover switch to operate the switching circuit portion.

In the endoscope, the changeover switch in the operating portion is operated to perform the switching of the image pick up units.

In a preferred aspect of the present invention, the endoscope is characterized in that the switching circuit portion is provided in the insertion portion.

In the endoscope, the switching circuit portion is electrically connected with the connector through the insertion portion, the operating portion, and the cable.

In a preferred aspect of the present invention, the endoscope is characterized in that the switching circuit portion is provided in the operating portion.

In the endoscope, the switching circuit portion is electrically connected with the connector through the operating portion and the cable.

In a preferred aspect of the present invention, the endoscope is characterized in that the switching circuit portion is coupled with the connector.

In the endoscope, the switching circuit portion is directly electrically connected with the connector.

In a preferred aspect of the present invention, the endoscope is characterized by further including a signal line electrically connecting the respective image pick up units with the switching circuit portion, and in that the switching circuit portion includes a flexible substrate bent to form an internal space, and the flexible substrate includes: a signal line connecting portion connected with a connection end of the signal line and provided to the flexible substrate such that the connection end of the signal line is arranged in the internal space; and an electronic part provided to the flexible substrate so as to be arranged in the internal space and to perform the switching.

In the endoscope, the connection end of the signal line and the electronic part are accommodated in the internal space formed by the flexible substrate.

In another aspect of the present invention, an endoscope system characterized by including an endoscope including: a plurality of image pick up units to pick up an observation image; a connector to be connected with an external device to perform signal processing; and a switching circuit portion electrically connected with the respective image pick up units and the connector and configured to switch the plurality of image pick up units so that one of the image pick up units transmits/receives a signal to/from the connector; and the external device to be connected with the connector to transmit/receive the signal, and to perform signal processing.

In a preferred aspect of the present invention, the endoscope system is characterized in that the endoscope further includes a changeover switch to operate the switching circuit portion.

In another aspect of the present invention, an endoscope is characterized by including: a plurality of image pick up units to pick up an observation image; a connector to be connected with an external device to perform signal processing; and a switching circuit portion coupled with the connector, electrically connected with the respective image pick up units and the connector, configured to switch the plurality of image pick up units so that one of the image pick up units transmits/receives at least one type of signal to/from the connector, and includes a shield to avoid occurrence of noise in a signal transmitted/received between the plurality of image pick up units and the external device.

In the endoscope, when one image pick up unit is used to obtain the observation image, the signal is transmitted/received between the one image pick up unit and the external device through the switching circuit portion, and the shield avoids noise from being produced in the signal in the switching circuit portion.

In a preferred aspect of the present invention, the endoscope is characterized in that the respective image pick up units transmit/receive a plurality of types of signals to/from the external device, and the shield avoids mutual interference between the plurality of types of signals in the switching circuit portion.

In the endoscope, the plurality of types of signals are transmitted/received between the one image pick up unit and the external device through the switching circuit portion, and the shield avoids mutual interference of the plurality of types of signals in the switching circuit portion.

In a preferred aspect of the present invention, the endoscope is characterized in that the plurality of types of signals include a high-frequency signal and a low-frequency signal, and the switching circuit portion includes a first relay circuit to switch the high-frequency signal and a second relay circuit to switch the low-frequency signal.

In the endoscope, between one image pick up unit and the external device, the high-frequency signal is transmitted/received through the first relay in the switching circuit portion and the low-frequency signal is transmitted/received through the second relay in the switching circuit portion.

In a preferred aspect of the present invention, the endoscope is characterized by further including a signal line electrically connecting each image pick up unit with the switching circuit portion, and in that the plurality of types of signals include a high-frequency signal and a low-frequency signal, the connector includes a connection pin to electrically connect the external device with the switching circuit portion, the switching circuit portion includes a flexible substrate with a plurality of surface portions wherein the signal line and the connection pin are connected to the plurality of surface portions, and the plurality of surface portions includes one surface portion wherein the signal line to transmit the high-frequency signal and the connection pin to transmit the high-frequency signal are connected to the one surface portion and a connection pattern provided in the one surface portion transmits the high-frequency signal.

In the endoscope, the high-frequency signal is transmitted/received between the one image pick up unit and the external device through only one of the plurality of surface portions of the flexible substrate in the switching circuit portion.

In a preferred aspect of the present invention, the endoscope is characterized by further including a signal line electrically connecting each image pick up unit with the switching circuit portion, and in that the plurality of types of signals include a high-frequency signal and a low-frequency signal, the connector includes a connection pin to electrically connect the external device with the switching circuit portion, and the signal line for the high-frequency signal is directly connected with the connection pin for the high-frequency signal in the switching circuit portion.

In the endoscope, the high-frequency signal is directly transmitted between the signal line and the connection pin in the switching circuit portion.

In a preferred aspect of the present invention, the endoscope is characterized in that the switching circuit portion includes a flexible substrate electrically connecting each image pick up unit with the connector, and the flexible substrate includes at least one inner layer including a connection pattern to transmit the signal, and a pair of outer layers for grounding sandwiching the inner layer.

In the endoscope, the electric field intensity in the connection pattern of the inner layer is increased by the outer layers for grounding.

In a preferred aspect of the present invention, the endoscope is characterized in that the shield shields an electromagnetic field from the outside.

In the endoscope, the signal is transmitted/received between one image pick up unit and the external device through the switching circuit portion, and the shield prevents the electromagnetic field from the outside from interfering with the signal in the switching circuit portion.

In a preferred aspect of the present invention, the endoscope is characterized by further including a signal line electrically connecting each image pick up unit with the switching circuit portion, the switching circuit portion includes a flexible substrate bent to form an internal space, and the flexible substrate includes: a signal line connecting portion connected with a connection end of the signal line and provided to the flexible substrate such that the connection end of the signal line is arranged in the internal space; and an electronic part provided to the flexible substrate so as to be arranged in the internal space and to perform the switching.

In the endoscope, the internal space is shielded by the flexible substrate from the external electromagnetic field, thereby preventing the external electromagnetic field from interfering with the signal in the connection end of the signal line and the electronic part accommodated in the internal space.

In another aspect of the present invention, a switching circuit member for an endoscope is characterized by configured to be coupled with a connector to be connected with an external device to perform signal processing, to be electrically connected with each of a plurality of image pick up units to pick up an observation image and the connector, and to switch the plurality of image pick up units so that one of the image pick up units transmits/receives at least one type of signal to/from the connector, and including a shield to avoid occurrence of noise in the signal transmitted/received between the plurality of image pick up units and the external device.

In a preferred aspect of the present invention, the switching circuit member for the endoscope is characterized in that each image pick up unit transmits/receives a plurality of types of signals to/from the external device, and the shield is to avoid mutual interference between the plurality of types of signals in the switching circuit member.

In a preferred aspect of the present invention, the switching circuit member for the endoscope is characterized in that the plurality of types of signals include a high-frequency signal and a low-frequency signal, and the switching circuit member includes a first relay circuit to switch the high-frequency signal and a second relay circuit to switch the low-frequency signal.

In a preferred aspect of the present invention, the switching circuit member for the endoscope is characterized in that the plurality of types of signals include a high-frequency signal and a low-frequency signal, the switching circuit member includes a flexible substrate including a plurality of surface portions wherein a signal line to electrically connect each image pick up unit with the switching circuit member and a connection pin to electrically connect the external device with the switching circuit member are to be connected to the plurality of surface portions, and the plurality of surface portions include one surface portion wherein the signal line to transmit the high-frequency signal and the connection pin to transmit the high-frequency signal are to be connected to the one surface portion and a connection pattern provided in the one surface portion is to transmit the high-frequency signal.

In a preferred aspect of the present invention, the switching circuit member for the endoscope is characterized in that the switching circuit member includes a flexible substrate to electrically connect each image pick up unit with the connector, and the flexible substrate includes at least one inner layer including a connection pattern to transmit the signal, and a pair of outer layers for grounding sandwiching the inner layer.

In a preferred aspect of the present invention, the switching circuit member for the endoscope is characterized in that the shield shields an electromagnetic field from the outside.

In a preferred aspect of the present invention, the switching circuit member for the endoscope is characterized in that the switching circuit member includes a flexible substrate bent to form an internal space, and the flexible substrate includes: a signal line connecting portion to be connected to a connection end of the signal line to electrically connect each image pick up unit with the switching circuit member and provided to the flexible substrate such that the connection end of the signal line is arranged in the internal space; and an electronic part provided to the flexible substrate so as to be arranged in the internal space and to perform the switching.

According to the endoscope of the present invention, in the endoscope, the structure that enables transmission/reception of the signal between the switching circuit portion and the external device does not have to be provided in accordance with each image pick up unit, the structure of the endoscope can be simplified to reduce the cost, and the external device does not have to be prepared in accordance with each image pick up unit, thereby forming the endoscope system that is simplified and has the reduced cost.

Further, according to the endoscope system of the present invention, the structure that enables transmission/reception of the signal between the switching circuit portion and the external device does not have to be provided in accordance with each image pick up unit, the structure of the endoscope can be simplified to reduce the cost, and the external device does not have to be prepared in accordance with each image pick up unit, the structure of the endoscope system can be simplified to reduce the cost.

BRIEF DESCRIPTION OF DRAWINGS

FIG. 1 is a schematic view showing an endoscope system according to a first embodiment of the present invention.

FIG. 2B is a block diagram showing a second image pick up unit in the endoscope according to the first embodiment of the present invention.

FIG. 2C is a view showing a timing chart of the second image pick up unit in the endoscope according to the first embodiment of the present invention.

FIG. 3 is a block diagram showing the endoscope system according to the first embodiment of the present invention.

FIG. 11 is a block diagram showing an endoscope system according to a sixth embodiment of the present invention.

FIG. 12 is a longitudinal cross-sectional view showing a connector in the endoscope according to the sixth embodiment of the present invention.

BEST MODE FOR CARRYING OUT THE INVENTION

Figure 2A:
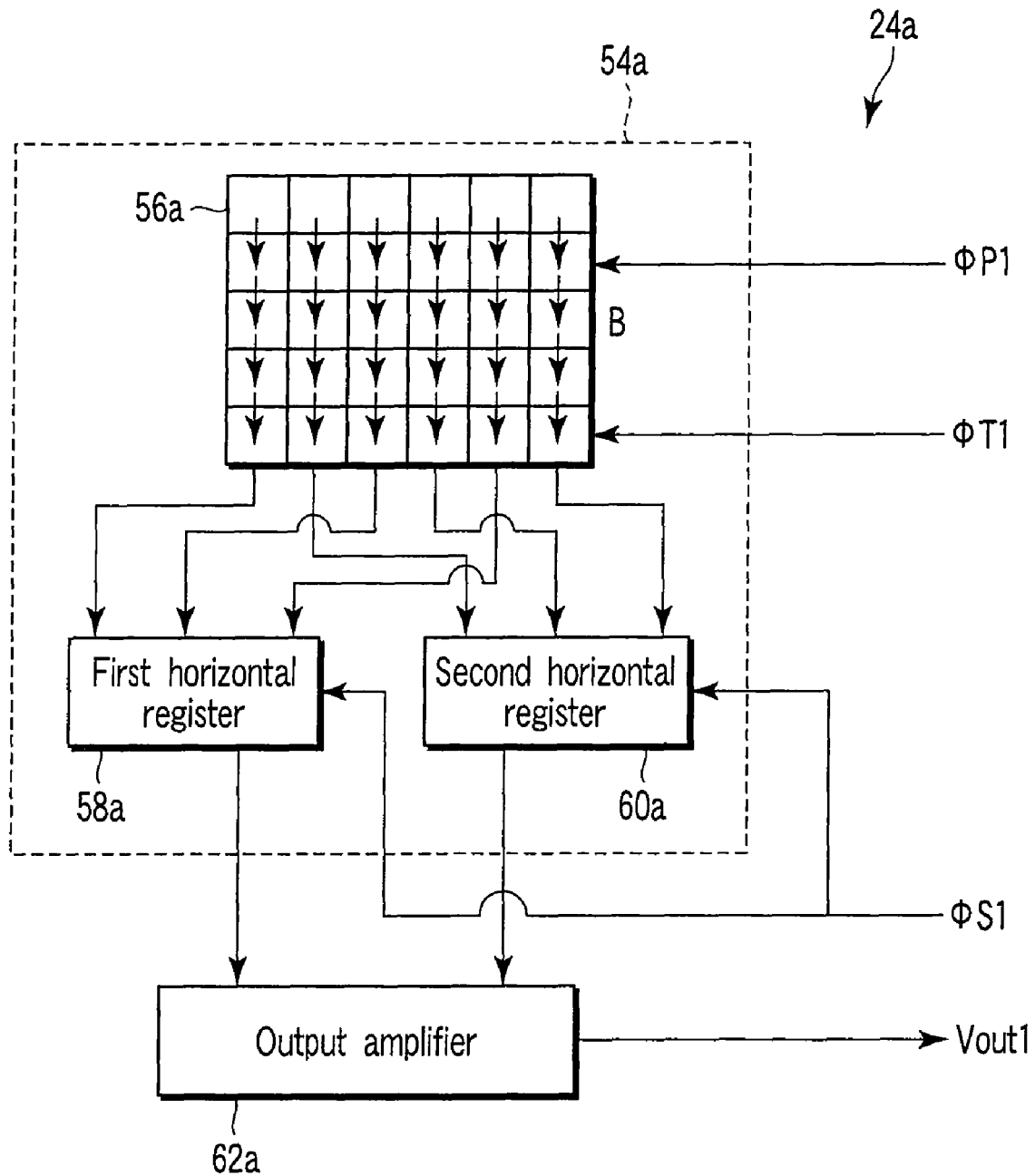
FIG. 2A is a block diagram showing a first image pick up unit in the endoscope according to the first embodiment of the present invention.

A first embodiment according to the present invention will now be explained hereinafter with reference to FIGS. 1 to 3. FIG. 1 shows an entire outline structure of an endoscope system 14 according to the embodiment. An endoscope 16 in the endoscope system 14 includes an elongated insertion portion 18 to be inserted into a body cavity. The insertion portion 18 is formed by sequentially coupling a distal end rigid portion 20 having rigidity, a bending portion 21 to be operated to be bent, and a long insertion tube portion 24 having flexibility from a distal end side.

A distal end opening 22 is formed at a distal end of the distal end rigid portion 20, and air or water is supplied to a diseased part in the body cavity therefrom and also an accessory to treat the diseased part protrudes therefrom.

Furthermore, a plurality of image pick up units to pick up observation images are arranged at the distal end of the distal end rigid portion 20. In the embodiment, a first image pick up unit 24a for normal optical observation and a second image pick up unit 24b for fluorescent observation are arranged side by side with each other at the distal end of the distal end rigid portion 20. Non-illustrated illumination lens to emit normal light for normal optical observation and excitation light for fluorescent observation is arranged side by side with the first and second image pick up units 24a and 24b.

On the other hand, a switching circuit portion 26 electrically connected with the first and second image pick up units 24a and 24b is accommodated on a rear end side of the distal end rigid portion 20. As will be explained later, the switching circuit portion 26 can switch the first and second image pick up units 24a and 24b so that one of the image pick up units 24a and 24b is connected with an electrical connector 28.

An operating portion 27 is coupled with a proximal end of the insertion portion 18. The operating portion 27 includes a distal-end-side grasping portion casing 30 grasped by an operator. An accessory inserting opening 32 is formed in the grasping portion casing 30 and the accessory is inserted into the accessory inserting opening 32. A first channel 34a is connected with an inner end of the accessory inserting opening 32, and the first channel 34a is inserted through the grasping portion casing 30 and the insertion portion 18 to be connected with a distal-end opening 22 of the distal end rigid portion 20. The accessory is inserted into the accessory inserting opening 32, inserted through the first channel 34a, and protruded from the distal end opening 22.

An operating portion casing 36 is integrally coupled with a rear end side of the grasping portion casing 30. An up-down bending knob 38a and a left-light bending knob 38b to operate the-bending portion 21 to be bent are coaxially supported on a side surface of the operating portion casing 36. The-bending portion 21 can be bent in four directions through the rotating operation of up-down bending knob 38a and left-light bending knob 38b. In the following explanation, the side of the operating portion casing 36 where the up-down bending knob 38a and the left-light bending knob 38b are arranged will be referred to as a front side.

An air supply/water supply switch 40 to operate air supply/water supply from the distal end opening 22 of the distal end rigid portion 20 is arranged in the operating portion casing 36. Additionally, a changeover switch 42 to activate the switching circuit portion 26 in the distal end rigid portion 20 is arranged side by side with the air supply/water supply switch 40 in the operating portion casing 36. Further, a universal cable 44 extends from the operating portion 27, and a connector portion 49 is arranged at an extending end of the universal cable 44.

An air supply/water supply connector 48 to be connected with an air supply/water supply device 47 is arranged in the connector portion 49. The second channel 34b is connected with an inner end of the air supply/water supply connecter 48, and the second channel 34b is inserted through the universal cable 44 and the operating portion 27 to join the first channel 34a in the grasping portion casing 30. Furthermore, through the operation of the air supply/water supply switch 40, air supply/water supply is carried out toward a diseased part from the air supply/water supply device 47 through the air supply/water supply connecter 48, the second and first channels 34b and 34a, and the distal end opening 22.

Moreover, a light source connector 52 to be connected with a light source device 50 is arranged in the connector portion 49. A light guide is connected with an inner end of the light source connector 52, and the light guide is inserted through the universal cable 44, the operating portion 27, and the insertion portion 18 to be connected with the illumination lens in the distal end rigid portion 20. Additionally, through the operation of the changeover switch 42 in the operating portion 27, the light source device 50 selectively generates one of normal right for normal optical observation and excitation light for fluorescent observation. Further, a diseased part is irradiated with normal right or excitation light from the light source device 50 through the light source connector 52, the light guide, and the illumination lens.

Furthermore, an electrical connector 28 electrically connected with the switching circuit portion 26 in the distal end rigid portion 20 is arranged in the connector portion 49. The electrical connector 28 is to be connected with a processor 46 as an external device to perform signal processing, through a scope cable 45.

The first and second image pick up units 24a and 24b according to the embodiment will now be explained in detail hereinafter. The first image pick up unit 24a for normal optical observation includes a first CCD 54a depicted in FIG. 2A. The first CCD 54a includes a group of two-dimensionally aligned pixels 56a to perform photoelectric conversion with respect to optical information image-formed on a light receiving surface stores the converted information as electric charges. One end column of the group of pixels 56a is connected with first and second horizontal registers 58a and 60a, and a direction toward the first and second horizontal registers 58a and 60a in the group of pixels 56a will be referred to as a vertical direction.

The electric charge stored in each pixel 56a is transferred by one pixel in the vertical direction every application of a first vertical transfer pulse signal ΦP1 having a low frequency of several kHz to several-hundred kHz (see an arrow group B in FIG. 2A). The electric charges transferred to a pixel column that is the endmost column in the vertical direction are divided and transferred to the first and second horizontal registers 58a and 60a in response to application of a first transfer gate pulse signal ΦT1 having a low frequency of several kHz to several-hundred kHz. The electric charges transferred to the first and second horizontal registers 58a and 60a are transferred in a horizontal direction perpendicular to the vertical direction in response to application of a first horizontal transfer pulse signal ΦS1 having a high frequency of 8 MHz or above, and output to an output amplifier 62a. The output amplifier 62a outputs a first image signal Vout1 in accordance with the input electric charges.

As shown in FIG. 2B, a second CCD 54b in the second image pick up unit 24b for fluorescent observation is a charge multiplying type CCD. In the CCD, as explained in U.S. Pat. No. 5,337,340 "Charge Multiplying Detector (CMD) suitable for small pixel CCD image sensors", through generation of an electric field having a sufficient intensity, conduction electrons collide with atoms to release electrons in a valence band and make the conduction electrons that have collided with the atoms escape from an atom collision region, and the ionization multiplies electric charges to improve the sensitivity. Further, in the CCD, adjusting amplitude and the number of pulses of a control pulse signal applied to the CCD enables freely controlling the sensitivity of the CCD.

In the second CCD 54b in the second image pick up unit 24b, like the first CCD 54a (see FIG. 2A), the electric charge stored in each pixel 56b is transferred by one pixel in the vertical direction by application of a second vertical transfer pulse signal ΦP2. The electric charges transferred to a pixel column that is the endmost column in the vertical direction are transferred to a horizontal register 59b.

As shown in a timing chart of FIG. 2C, after application of the second vertical transfer pulse signal ΦP2, when a second horizontal transfer pulse signal ΦS2a or ΦS2b (which will be generically referred to as ΦS2 hereinafter) is applied to the second horizontal register 59b, the electric charges transferred to the horizontal register 59b are transferred to the output amplifier 62b in the horizontal direction from the horizontal register 59b in synchronization with the second horizontal transfer pulse signal ΦS2. It is to be noted that a sensitivity multiplication mechanism is provided in the horizontal register 59b, and adjusting amplitude and the number of pulses of a control pulse signal ΦCMD2 to be applied to the sensitivity multiplication mechanism enables changing the sensitivity of the second CCD 54b from onefold to several-hundred-fold. Furthermore, when a second reset pulse signal ΦRS2 is applied to the output amplifier 62 an image signal ΦVout2 is output from the output amplifier 62.

A control system of the endoscope system 14 according to the embodiment will now be explained. It is to be noted that the second control pulse signal ΦCMD2 is not switched by the switching circuit portion 26, thereby omitting an explanation thereof.

Referring to FIG. 3, when the air supply/water supply switch 40 in the endoscope 16 is operated, an air supply/water supply signal ΦSW1 is output to the air supply/water supply device 47, thereby activating the air supply/water supply device 47. Moreover, when the changeover switch 42 in the endoscope 16 is operated, the endoscope system 14 is switched between a normal optical observation mode of using the first image pick up unit 24a to obtain a normal optical observation image and a fluorescent observation mode of using the second image pick up unit 24b to obtain a fluorescent observation image.

That is, when the changeover switch 42 is operated for switching, a switching signal ΦSW2 is output to each of the light source device 50, an information relay circuit 64, and first and second relay circuits 66a and 66b in the switching circuit portion 26. Additionally, illumination light supplied to the endoscope 16 from the light source device 50 is switched between normal right and excitation light, and the information relay circuit 64, the first relay circuit 66a, and the second relay circuit 66b are switched between the first image pick up unit 24a side and the second image pick up unit 24b side. It is to be noted that the endoscope system 14 is in the normal optical observation mode at the time of starting the endoscope system 14.

In the normal optical observation mode, a first information signal ΦD1 is output from a first CCD information storage portion 68a to a driving circuit 70 in the processor 46 through the information relay circuit 64 switched to the first image pick up unit 24a side.

The driving circuit 70 that has received the first information signal ΦD1 outputs a first vertical transfer pulse signal ΦD1 to the first image pick up unit 24a through the second relay circuit 66b switched to the first image pick up unit 24a side. Further, the driving circuit 70 outputs a first transfer gate pulse signal ΦT1 to the first image pick up unit 24a through the first relay circuit 66a switched to the first image pick up unit 24a side. Furthermore, the driving circuit 70 outputs a first horizontal transfer pulse signal ΦS1 to the first image pick up unit 24a through the first relay circuit 66a.

Thereafter, the first image pick up unit 24a outputs a first image signal Vout1 to a image processing circuit 72 in the processor 46 through the second relay circuit 66b switched to the first image pick up unit 24a side. The image processing circuit 72 that has received the first image signal Vout1 performs signal processing to display a normal optical observation image on the monitor 74.

On the other hand, in the fluorescent observation mode, a second CCD information storage portion 68b outputs a second information signal ΦD2 to the driving circuit 70 in the processor 46 through the information relay circuit 64 switched to the second image pick up unit 24b side. In the embodiment, the first information signal ΦD1 is an H level signal and the second information signal ΦD2 is an L level signal.

Like the normal optical observation mode, the driving circuit 70 outputs a second vertical transfer pulse signal ΦP2 to the second image pick up unit 24b through the second relay circuit 66b switched to the second image pick up unit 24b side. Furthermore, the driving circuit 70 outputs a second horizontal transfer pulse signal ΦS2 and a second reset pulse signal ΦRS2 to the second image pick up unit 24b through the first relay circuit 66a switched to the second image pick up unit 24b side.

Thereafter, the second image pick up unit 24b outputs a second image signal Vout2 to the image processing circuit 72 in the processor 46 through the second relay circuit 66b switched to the second image pick up unit 24b side. The image processing circuit 72 displays a fluorescent observation image on the monitor 74.

A function of the endoscope system 14 according to the embodiment will now be explained. When performing observation using the endoscope system 14 according to the embodiment, the connector portion 49 in the endoscope 16 is connected with the air supply/water supply device 47 and the light source device 50, and the connector portion 49 is connected with the processor 46 through the scope cable 45. The air supply/water supply device 47, the light source device 50, and the processor 46 are started. At the time of starting, the endoscope system 14 is in the normal optical observation mode, the light source device 50 produces normal right, and the information relay circuit 64 and the first and second relay circuits 66a and 66b in the endoscope 16 are switched to the first image pick up unit 24a side.

The insertion portion 18 of the endoscope 16 is inserted into a body cavity so that the distal end rigid portion 20 faces a diseased part in the body cavity. The normal right is supplied to the diseased part from the light source device 50 through the light source connector 52, the light guide, and the illumination lens, and the diseased part is illuminated with the normal right. Moreover, the first information signal ΦD1 is input from the first CCD information storage portion 68a to the driving circuit 70 in the processor 46 through the information relay circuit 64, and the driving circuit 70 drives the first image pick up unit 24a. Additionally, the first image signal Vout1 is output from the first image pick up unit 24a to the image processing circuit 72 in the processor 46, thereby displaying a normal optical observation image on the monitor 74. An operator performs a diagnostic, a treatment, and others while observing the normal optical observation image on the monitor 74. Through the operation of the air supply/water supply switch 40, air supply/water supply to the diseased part is performed as required.

When the operator wants to diagnose the diseased part based on fluorescent observation in more detail, the operator operates the changeover switch 42 to switch the endoscope system 14 to the fluorescent observation mode. When the changeover switch 42 is operated, the light source device 50 emits excitation light, and the diseased part is irradiated with the excitation light through the light source connector 52, the light guide, and the illumination lens.

Further, the information relay circuit 64 and the first and second relay circuits 66a and 66b in the endoscope 16 are switched to the second image pick up unit 24b side. Furthermore, the second information signal ΦD2 is output from the second CCD information storage portion 68b to the driving circuit 70 in the processor 46 through the information relay circuit 64. Moreover, the second image pick up unit 42b is operated by the driving circuit 70, thereby displaying a fluorescent observation image on the monitor 74.

When the excitation light is applied, since a cancerous tissue or the like absorbs the excitation light to emit fluorescence having a higher intensity than that of a normal tissue, using the fluorescent observation image enables diagnosing the diseased part in more detail.

Therefore, the endoscope system 14 according to the embodiment includes the following effect. In the endoscope system 14 according to the embodiment, the switching circuit portion 26 is electrically connected with the first and second image pick up units 24a and 24b and the electrical connector 28, and can switch the first and second image pick up units 24a and 24b so that one of the image pick up units 24a and 24b transmits/receives a signal to/from the electrical connector 28. Therefore, a structure to enable signal transmission/reception between the switching circuit portion 26 and the electrical connector 28 does not have to be provided in accordance with each of the first and second image pick up units 24a and 24b, and the scope cable 45 and the processor 46 do not have to prepared in accordance with each of the first and second image pick up units 24a and 24b. Accordingly, the structures of the endoscope 16 and the endoscope system 14 are simplified, thereby reducing a cost.

Further, since the changeover switch 42 to operate the switching circuit portion 26 is arranged in the endoscope 16, the operability of the changeover switch 42 is improved as compared with an example where the changeover switch 42 is arranged in, e.g., the processor 46. In particular, since the changeover switch 42 is arranged in the operating portion 27 to be grasped by an operator and includes the air supply/water supply switch 40, the left-light bending knob 38b, and others collectively arranged therein, the endoscope 16 does not have to be again grasped when operating the changeover switch 42, thereby sufficiently improving the operability.

Furthermore, the switching circuit portion 26 is accommodated on a rear end side of the distal end rigid portion 20. Therefore, a structure that enables signal transmission/reception between the switching circuit portion 26 and the electrical connector 28 does not have to be provided from the rear end of the distal end rigid portion 20 to the electrical connector 28 in the connector portion 49 over the substantially entire length of the endoscope 16 in accordance with each of the first and second image pick up units 24a and 24b, thus sufficiently simplifying the structure of the endoscope 16.

Moreover, the information relay circuit 64 can switch the first and second CCD information storage portions 68a and 68b so that one of the first and second CCD information storage portions 68a and 68b transmit the information signals ΦD1 and ΦD2 to the electrical connector 28, and the electrical connector 28 outputs one of the information signal ΦD1 or ΦD2 from the electrical connector 28 to the processor 46. Here, when the information relay circuit 64 is not used, the information signals ΦD1 and ΦD2 are transmitted from the endoscope 16 to the processor 46 through two routes for the first information signal ΦD1 and the second information signal ΦD2. Since a conventional processor for an endoscope using a single image pick up unit receives the information signal through a single route, the processor cannot be used. In the embodiment, the conventional processor for endoscope using the single image pick up unit can be utilized as it is, thus improving the interchangeability of the endoscope system 14.

A second embodiment according to the present invention will now be explained hereinafter. Like reference numerals denote structures having the same functions as those in the first embodiment, thereby omitting an explanation thereof. In the endoscope system 14 according to the embodiment, the switching circuit portion 26 is arranged in the insertion tube portion 24 of the endoscope 16. Therefore, a length of the distal end rigid portion 20 in a longitudinal direction of the insertion portion 18 is smaller than that in the first embodiment, thereby improving insertion properties of the endoscope 16.

Figure 4:
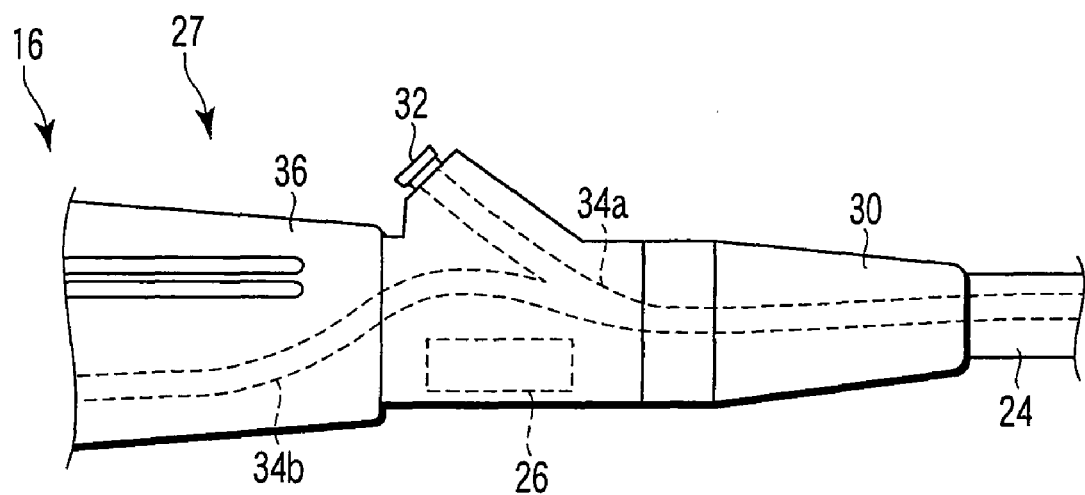
FIG. 4 is a perspective view showing an operating portion in an endoscope according to a third embodiment of the present invention.

FIG. 4 shows a third embodiment according to the present invention. Like reference numerals denote structures having the same functions as those in the first embodiment, thereby omitting an explanation thereof. In the embodiment, the switching circuit portion is arranged in the grasping portion casing 30 of the operating portion 27.

That is, the first channel 34a extending from the insertion portion 18 is inserted into the grasping portion casing 30, and the first channel 34a is connected with the inner end of the accessory insertion opening 32 formed in the grasping portion casing 30. Additionally, the first channel 34a diverges to the second channel 34b in the grasping portion casing 30, and the second channel 34b is inserted into the operating portion casing 36 in the operating portion 37. In the grasping portion casing 30, the switching circuit portion 26 is fixed on an inner wall surface opposing to the accessory insertion opening 32.

That is, in the grasping portion casing 30, the first and second channels 34a and 34b are arranged on the accessory insertion opening 32 side, and the switching circuit portion 26 is arranged on the opposite side.

Therefore, the endoscope system 14 according to the embodiment includes the following effect. In the embodiment, the switching circuit portion 26 is not arranged in the insertion portion 18 of the endoscope 16, and a diameter of the insertion portion 18 can be reduced.

Figure 5A:
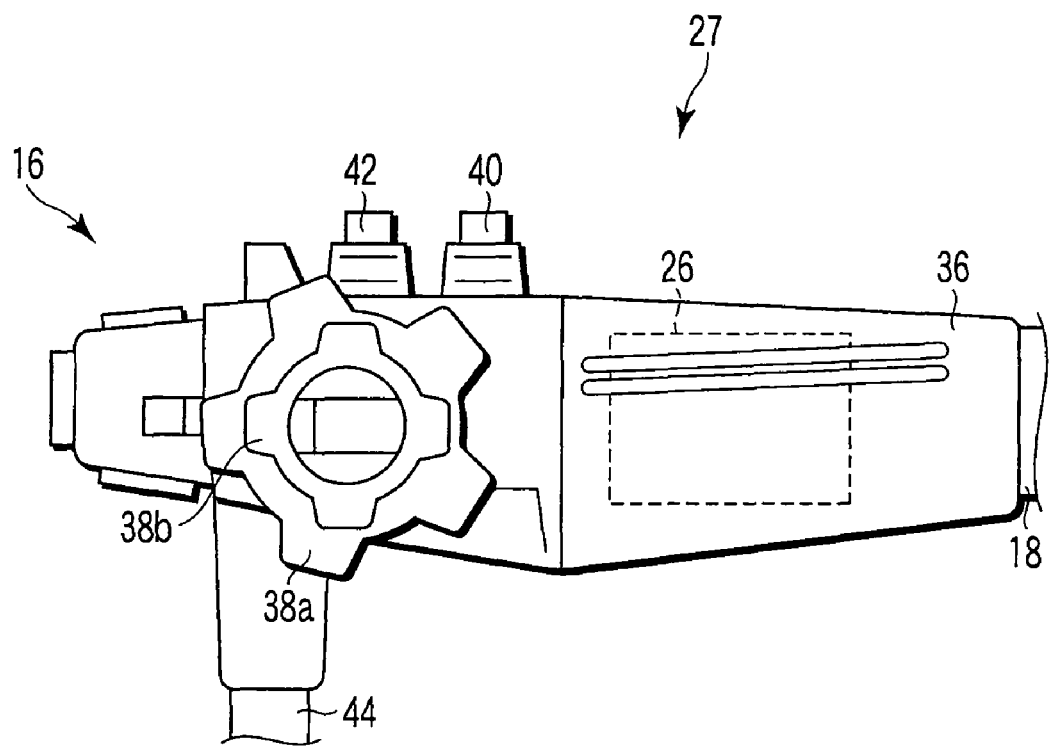
FIG. 5A is a perspective view showing an operating portion in an endoscope according to a fourth embodiment of the present invention.
Figure 5B:
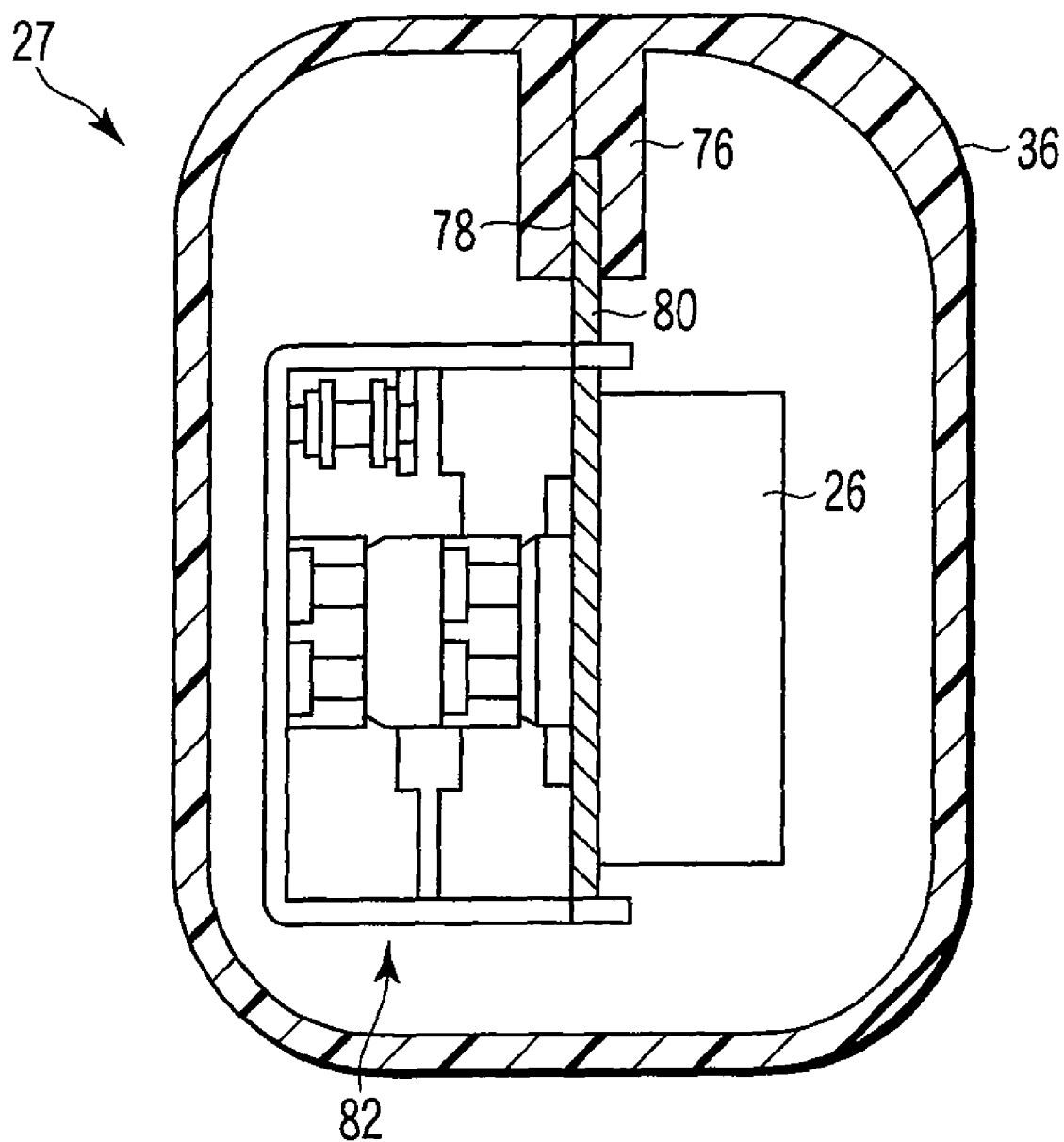
FIG. 5B is a transverse cross-sectional view showing the operating portion in the endoscope according to the fourth embodiment of the present invention.

FIGS. 5A and 5B show a fourth embodiment according to the present invention. Like reference numerals denote structures having the same functions as those in the third embodiment, thereby omitting an explanation thereof. In the embodiment, the switching circuit portion 26 is arranged in the operating portion casing 36 of the operating portion 27.

A locking portion 76 protruding toward a lower wall extends in a longitudinal direction of the operating portion 27 on an inner surface of an upper wall of the operating portion casing 36. A locking groove 78 extends in the longitudinal direction of the operating portion 27 in a lower end surface of the locking portion 76. A tabular frame 80 is fitted and fixed in the locking groove 78, and the frame 80 is arranged substantially parallel with both side surfaces of the operating portion casing 36 to define a front space and a rear space in the operating portion casing 36.

Meanwhile, the bending portion 21 (see FIG. 1) of the endoscope 16 is formed by coaxially coupling cylindrical bending parts rotatably with each other, and the-bending portion 21 (see FIG. 1) is operated to be bent by moving forward and backward an operation wire that is connected with the endmost-bending portion and inserted through the insertion portion 18 and the operating portion 27.

An angle mechanism 82 to convert a rotating operation to the up-down bending knob 28a and the left-light bending knob 38b into a forward/backward movement operation to move the operation wire forward/backward is accommodated in the operating portion casing 36. The angle mechanism 82 is fixed on a front surface of the frame 80 in the operating portion casing 36, and arranged in the front space in the operating portion casing 36 over a substantially entire length of the operating portion 27 in a longitudinal direction.

On the other hand, the switching circuit portion 26 is fixed on a rear surface of the frame 80 in the operating portion casing 36, and arranged in the rear space in the operating portion casing 36 on a distal end side of the operating portion casing 36.

Therefore, the endoscope system 14 according to the embodiment includes the following effect. In the embodiment, since the switching circuit portion 26 is arranged on the rear side rather than the front side where the angle mechanism 82 is arranged in the operating portion casing 36, the switching circuit portion 26 does not obstruct the forward/backward movement operation of the operation wire, and the forward/backward movement operation of the operation wire can be assuredly performed.

FIGS. 6 to 10B show a fifth embodiment according to the present invention. Like reference numerals denote structures having the same functions as those in the first embodiment, thereby omitting an explanation thereof. In the endoscope system according to the embodiment, the switching circuit portion is provided to the electrical connector in the connector portion.

Figure 6:
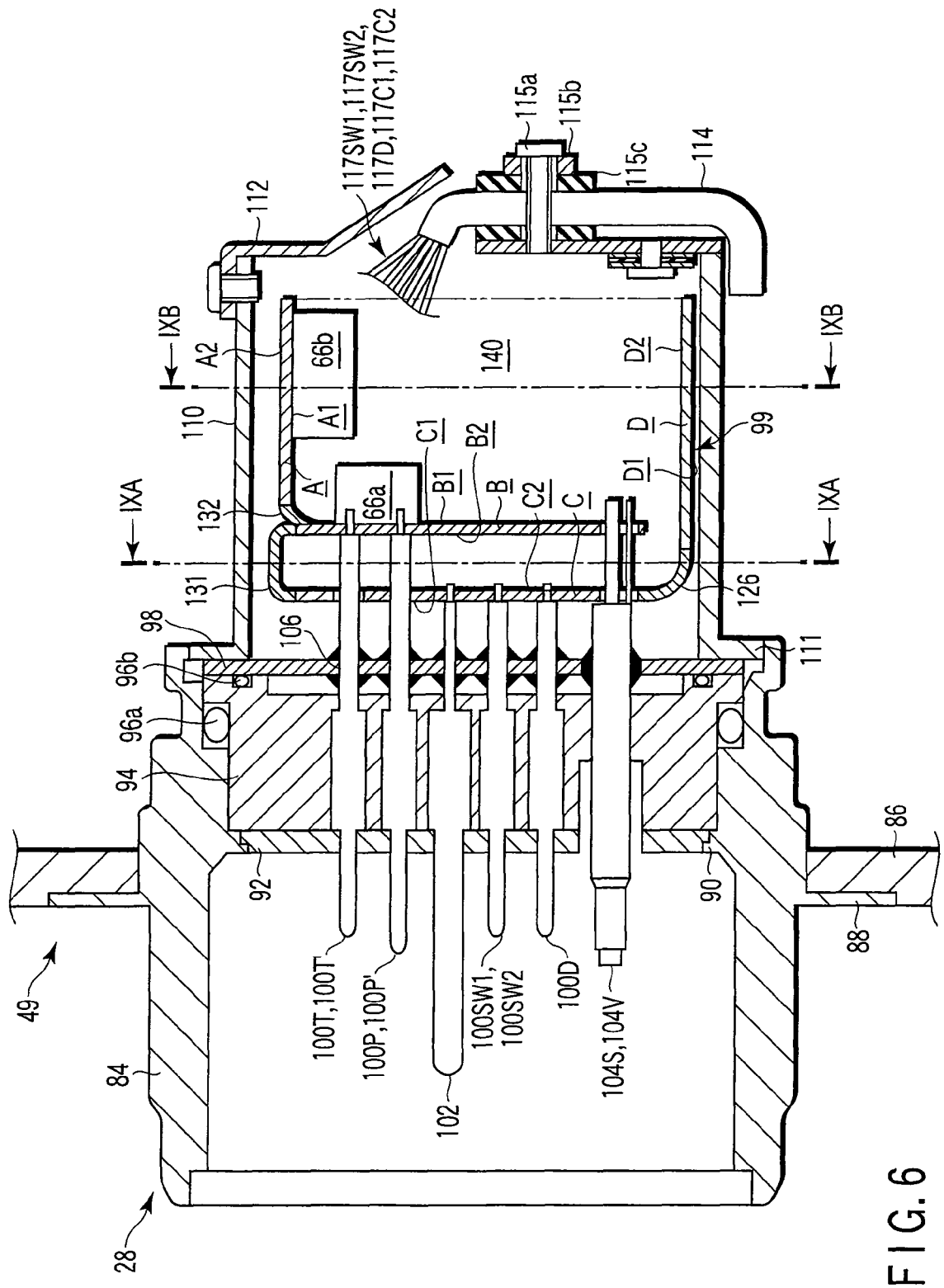
FIG. 6 is a longitudinal cross-sectional view showing a connector in an endoscope according to a fifth embodiment of the present invention.
Figure 7:
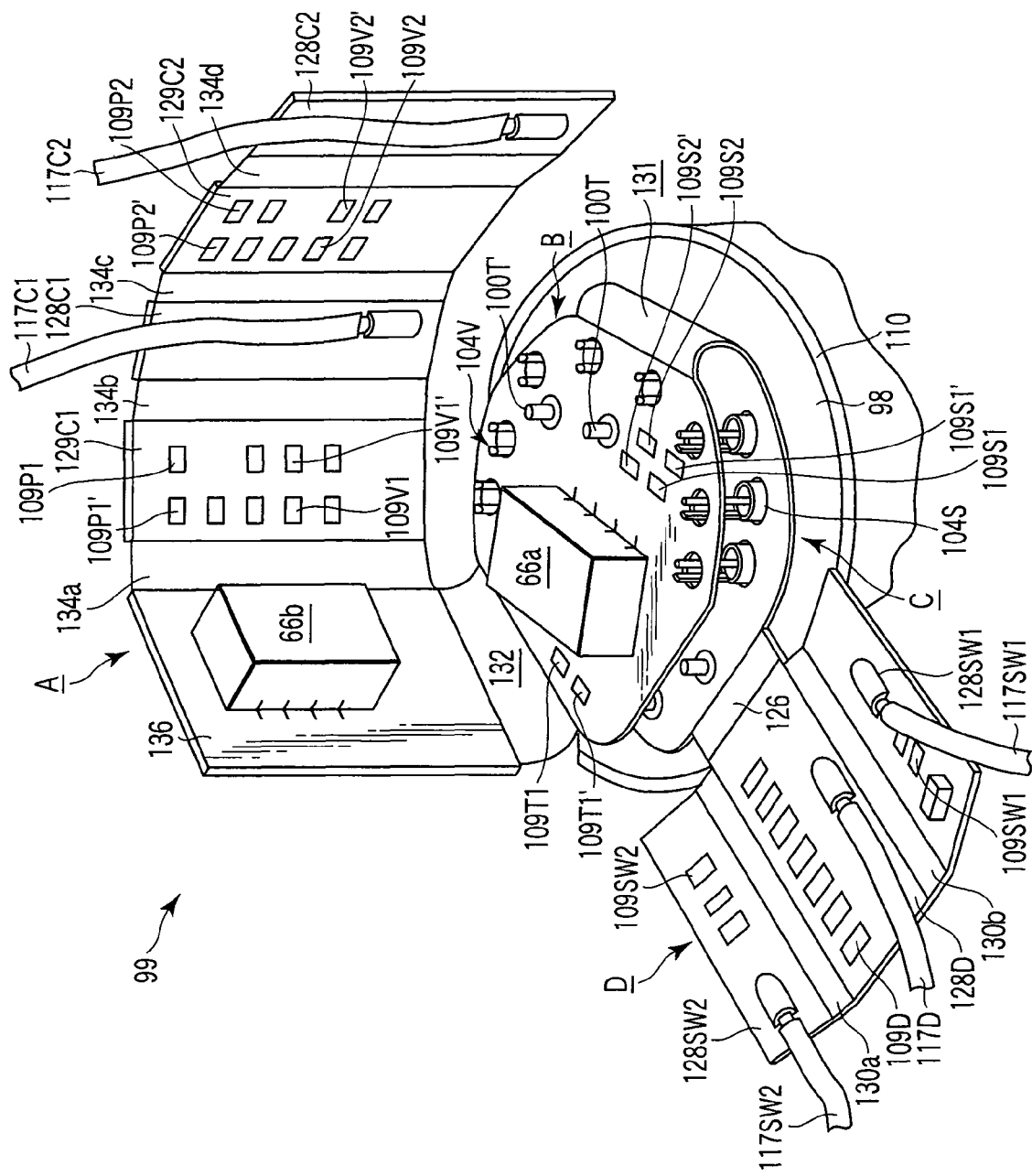
FIG. 7 is an assembling view showing a flexible substrate in the endoscope according to the fifth embodiment of the present invention.
Figure 8A:
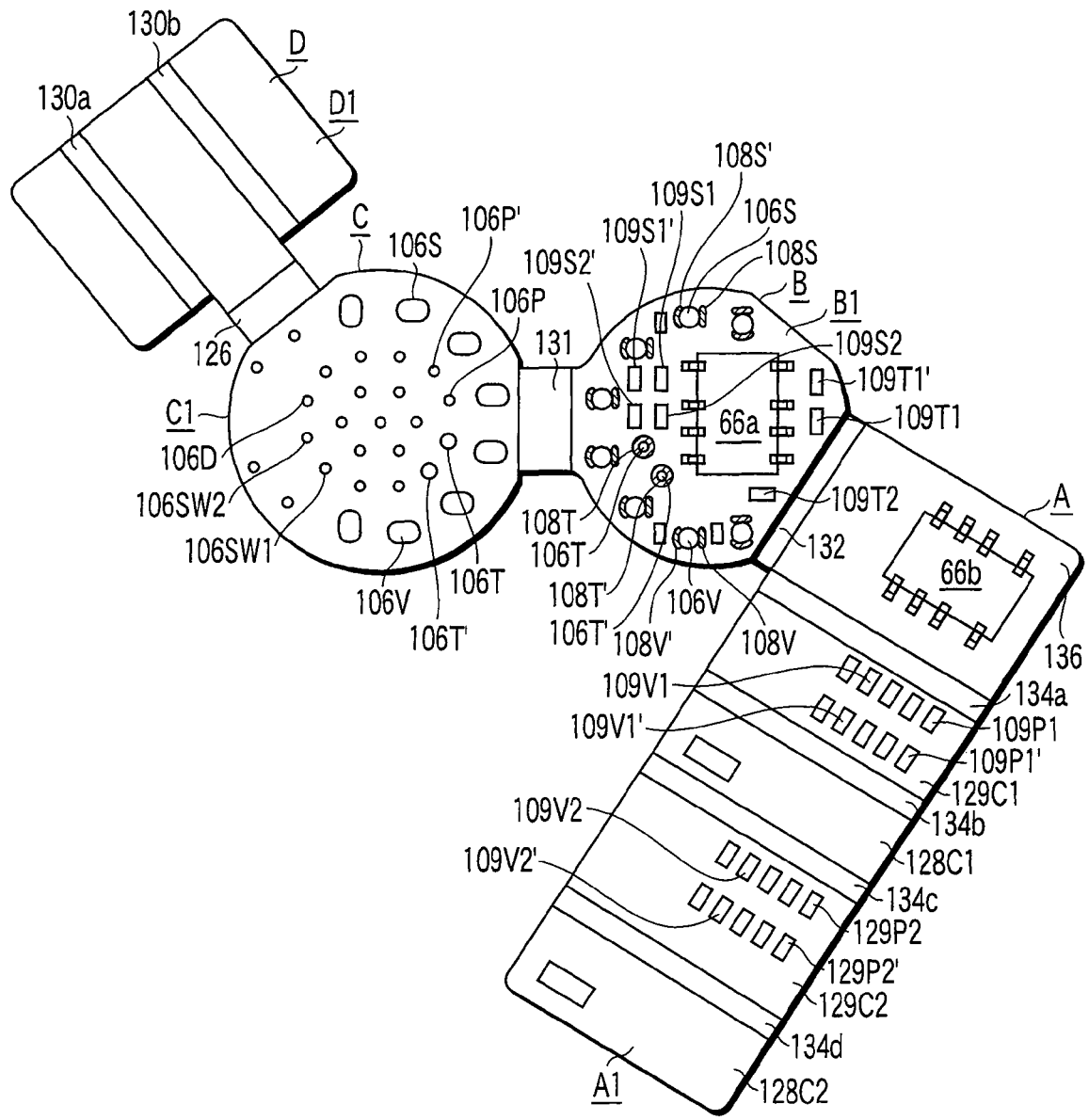
FIG. 8A is a development view showing a front surface of the flexible substrate in the endoscope according to the fifth embodiment of the present invention.
Figure 8B:
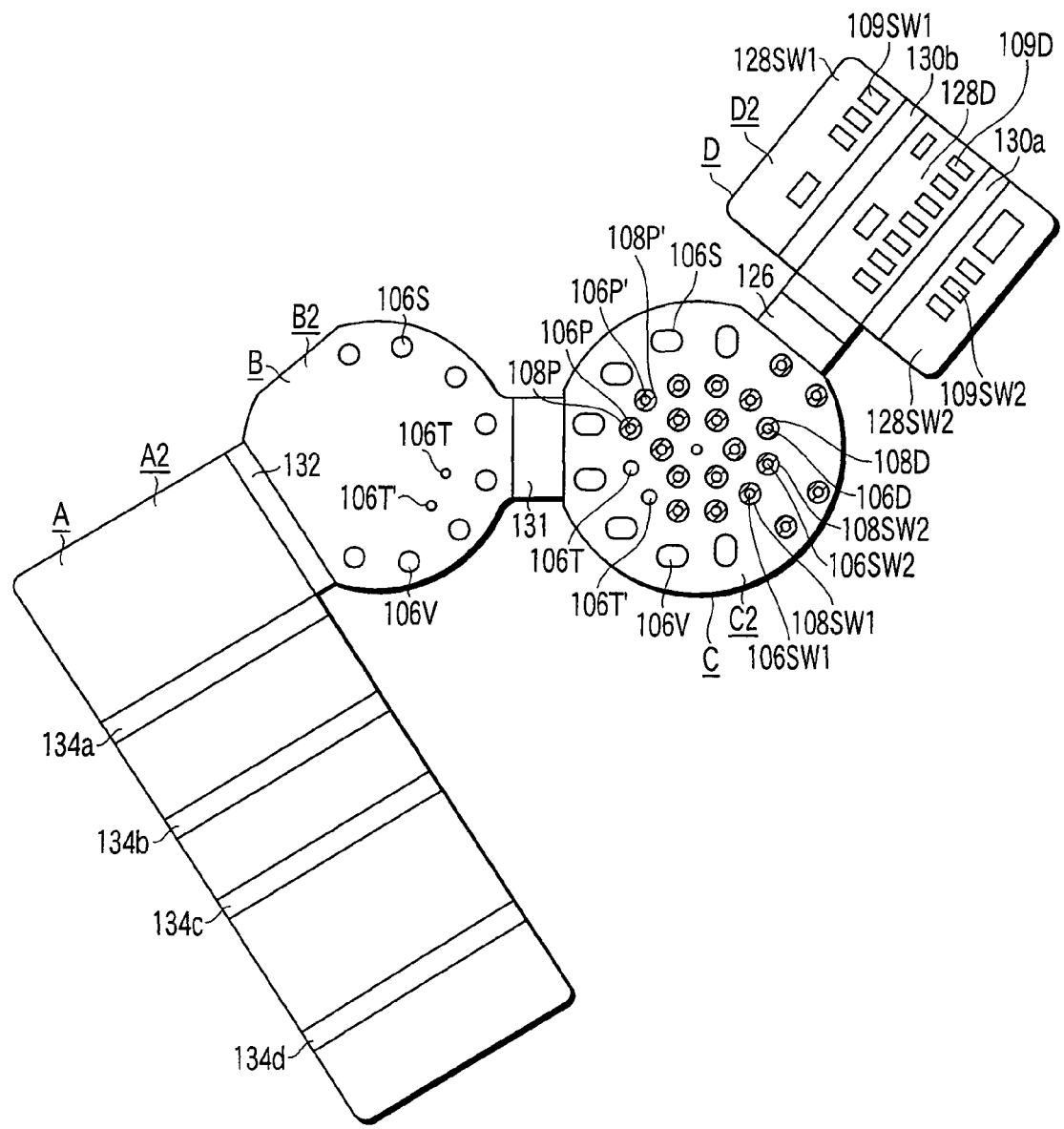
FIG. 8B is a development view showing a rear surface of the flexible substrate in the endoscope according to the fifth embodiment of the present invention.

As shown in FIG. 6, the electrical connector 28 according to the embodiment includes a connecter 84 protruding from the connector portion 49. The connecter 84 has electroconductive properties and a substantially cylindrical shape, and is fitted in a circular opening formed in a connector case 86 as a housing of the connector portion 49. Further, a first flange portion 88 is formed on an outer periphery of the connecter 84, and the first flange portion 88 is brought into contact with and screwed to the connector case 86, thereby fixing the connecter 84 to the connector case 86.

A locking convex portion 90 is formed on an inner peripheral surface of the connecter 84 over an entire circumference, and a substantially disk-shaped cover member 92 is fitted into an inside space of the connecter 84 from an inner opening and comes into contact with and fixed to the locking convex portion 90 by using an adhesive. Furthermore, a substantially cylindrical insulative insulator 94 is fitted from the inner opening of the connecter 84 and comes into contact with and fixed on an inner face of the cover member 92 by using an adhesive. It is to be noted that the insulator 94 and the connecter 84 are bonded and fixed to each other through a first packing 96a, and a space between the insulator 94 and the connecter 84 is water-tightly maintained. Moreover, a click-shaped substrate 98 is bonded and fixed to an inner face of the insulator 94 through a second packing 96b, and a space between the insulator 94 and the substrate 98 is water-tightly maintained.

A plurality of single-wire pins 100T, ..., 100D, a post pin 102, and a plurality of coaxial pins (Burndy) 104S and 104V pierce the cover member 92, the insulator 94, and the substrate 98. Outer end sides of the single-wire pins 100T, ..., 100D and the coaxial pins 104S and 104V protrude outwards from the cover member 92 to be connected with a scope cable 45 (see FIG. 3). Moreover, an outer end side of the post pin 102 protrudes outward beyond the outer ends of the single-wire pins 100T, ..., 100D and the coaxial pins 104S and 104V. When the operator puts hand into the connecter 84, the post pin 102 comes into contact with a hand of an operator before the single-wire pins 100T, ..., 100D and the coaxial pins 104S and 104V to discharge static electricity of the operator.

The single-wire pins 100T, ..., 100D, the post pin 102, and the coaxial pins 104S and 104V are bonded and fixed to the insulator 94. Additionally, inner end sides of the single-wire pins 100T, ..., 100D, the post pin 102, and the coaxial pins 104S and 104V are inserted into a through hole 106 of the substrate 98 and soldered in the through hole 106 of the substrate 98. Further, the inner end sides of the single-wire pins 100T, ..., 100D and the coaxial pins 104S and 104V protrude from the substrate 98 to extend into an electroconductive shield tube 110 arranged on an inner face side of the substrate 98 coaxially with the connecter 84.

A second flange portion 111 is formed at a substrate 98 side end of the shield tube 110, a male screw formed on an outer peripheral surface of the second flange portion 111 is screwed to a female screw formed at an inner end on an inner peripheral surface of the connecter 84. Furthermore, by screwing the shield tube 110 into the connecter 84, a rim of the substrate 98 comes into contact with the second flange portion 111 of the shield tube 110, and a ground land formed on the rim of the substrate 98 is electrically connected with the shield tube 110. Moreover, the shield tube 110 and the connecter 84 are electrically connected with each other through a screw portion.

On the other hand, an electroconductive shield lid 112 covering an inner end opening of the shield tube 110 is screwed at the inner end of the shield tube 110. A transmission cable 114 extending from a universal cable 44 (see FIG. 1) is fixed to the shield lid 112 by means of a fixing plate 115b attached to the shield via a screw 115a, through a fixing rubber 115c. A distal end of the transmission cable 114 is inserted into the shield tube 110 through an opening formed in the shield lid 112. The transmission cable 114 inserted into the shield lid 110 is electrically connected with the single-wire pins 100T, . . . , 100D and the coaxial pins 104S and 104V through a flexible substrate 99.

Electrical connection achieved between the transmission cable 114 and the single-wire pins 100T, . . . , 100D and the coaxial pins 104S and 104V through the flexible substrate 99 will now be explained in detail. Referring to FIGS. 3 and 6, an air supply/water supply cable 117SW1 extending from an air supply/water supply switch 40, a switching cable 117SW2 extending from a changeover switch 42, an information cable 117D extending from an information relay circuit 64, a first imaging cable 117C1 extending from a first image pick up unit 24a, and a second imaging cable 117C2 extending from a second image pick up unit 24b are inserted through the transmission cable 114.

An air supply/water supply signal line, a switching signal line, and an information signal line as single electric wires to transmit respectively an air supply/water supply signal ΦSW1, a switching signal ΦSW2, and information signals ΦD1 and ΦD2 are respectively inserted through the air supply/water supply cable 117SW1, switching cable 117SW2 and information cable 117D.

Additionally, a first vertical transfer pulse signal line, a first horizontal transfer pulse signal line, a first transfer gate pulse signal line, and a first image signal line as coaxial wires to transmit respectively a first vertical transfer pulse signal ΦP1, a first horizontal transfer pulse signal ΦS1, a first transfer gate pulse signal ΦT1, and a first image signal Vout1 are inserted through the first imaging cable 117C1. A second vertical transfer pulse signal line, a second horizontal transfer signal pulse line, a second reset pulse signal line, and a second image signal line are inserted through the second imaging cable 117C2.

On the other hand, single-wire pins include an air supply/water supply signal single-wire pin 100SW1, a switching signal single-wire pin 100SW2, and an information signal single-wire pin 100D. Furthermore, single-wire pins include a pair of vertical transfer pulse signal single-wire pins 100P and 100P' and a pair of transfer gate pulse/reset pulse signal single-wire pins 100T and 100T'. Here, of a pair of single-wire pins, one single-wire pin is used for a signal, and the other single-wire pin is used for grounding. Moreover, coaxial pins include a horizontal transfer signal coaxial pin 104S and a image signal coaxial pin 104V.

Referring to FIGS. 6 to 8B, the flexible substrate 99 is formed by sequentially coupling an A-surface portion, a B-surface portion, a C-surface portion, and a D-surface portion. In the following explanation, front sides of the A-surface portion, the B-surface portion, the C-surface portion, and the D-surface portion will be referred to as an A1-surface, a B1-surface, a C1-surface, and a D1-surface, and rear sides of the same will be referred to as a A2-surface, a B2-surface, a C2-surface, and a D2-surface.

The C1-surface (see FIG. 8A) of the flexible substrate 99 is arranged to face the substrate 98 of the connecter 84. An air supply/water supply signal through hole 106SW1, a switching signal through hole 106SW2, and an information signal through hole 106D are bored from the C1-surface to the C2-surface on the opposite side (see FIG. 8B), and the air supply/water supply signal single-wire pin 100SW1, the switching signal single-wire pin 100SW2, and the information signal single-wire pin 100D are respectively inserted into the holes from the C1-surface side to the C2-surface side.

On the C2-surface, an air supply/water supply signal pin land 108SW1, a switching signal pin land 108SW2, and an information signal pin land 108D are respectively formed around the air supply/water supply signal through hole 106SW1, the switching signal through hole 106SW2, and the information signal through hole 106D, and the air supply/water supply signal single-wire pin 100SW1, the switching signal single-wire pin 100SW2, and the information signal single-wire pin 100D are respectively soldered to the pin lands. The air supply/water supply signal pin land 108SW1, the switching signal pin land 108SW2, and the information signal pin land 108D are respectively electrically connected with an air supply/water supply signal connection land 109SW1, a switching signal connection land 109SW2, and an information signal connection land 109D on the D2-surface through a connection pattern in the flexible substrate 99 between the C2-surface and the D2-surface (see FIG. 8B).

A CD-bending portion 126 is arranged between the C2-surface and the D2-surface, and the D-surface portion is arranged to be substantially vertical to the C-surface portion with the D2-surface facing a central axis of the electrical connector 28 through bending the CD-bending portion 126. Additionally, the D-surface portion includes first and second D-bending portions 130a and 130b extending substantially parallel to each other and nearly vertical to the C-surface portion.

The first and second D-bending portions 130a and 130b divide the D2-surface into an information cable connecting portion 128D coupled with the CD-bending portion 126, and an air supply/water supply cable connecting portion 128SW1 and a switching cable connecting portion 128SW2 respectively arranged on lateral sides of the information cable connecting portion 128D. The air supply/water supply cable 117SW1 is connected with the air supply/water supply cable connecting portion 128SW1, and the air supply/water supply signal line extending from the air supply/water supply cable 117SW1 is soldered to the air supply/water supply signal connection land 109SW1 arranged at the air supply/water supply cable connecting portion 128SW1. The switching cable connecting portion 128SW2 and the information cable connecting portion 128D is also similar to this. Moreover, the D-surface portion is arranged along an outer periphery of the C-surface portion through bending the first and second D-bending portion 130a and 130b.

On the other hand, a horizontal transfer pulse signal through hole 106S and a pair of transfer gate pulse/reset pulse signal through holes 106T and 106T' are bored from the C1-surface to the C2-surface, and the horizontal transfer pulse signal coaxial pin 104S and the pair of transfer gate pulse/reset pulse signal single-wire pins 100T and 100T' are respectively inserted into the through holes from the C1-surface side to the C2-surface side and protrude toward the B2-surface (see FIG. 8B) arranged to face the C2-surface.

The B2-surface is arranged substantially parallel with the C2-surface with a distance between itself and the C2-surface through bending a CB-bending portion 131 between the C2-surface and the B2-surface. The horizontal transfer pulse signal through hole 106S and the pair of transfer gate pulse/reset pulse signal through holes 106T and 106T' are also respectively formed in the B2-surface in alignment with the horizontal transfer pulse signal through hole 106S and the pair of transfer gate pulse/reset pulse signal through holes 106T and 106T' in the C2-surface.

The horizontal transfer pulse signal through hole 106S and the pair of transfer gate pulse/reset pulse signal through holes 106T and 106T' are bored from the B2-surface to the B1-surface (see FIG. 8A), and the horizontal transfer pulse signal coaxial pin 104S and the pair of transfer gate pulse/reset pulse signal single-wire pins 100T and 100T' are respectively inserted into the through holes from the B2-surface side toward the B1-surface side.

On the B1-surface, a pair of horizontal transfer pulse signal pin lands 108S and 108S' are formed around the horizontal transfer pulse signal through hole 106S, and the horizontal transfer pulse signal coaxial pin 104S is soldered to the pin lands. Further, transfer gate pulse/reset pulse signal pin lands 108T and 108T' are formed around the pair of transfer gate pulse/reset pulse signal through holes 106T and 106T', and the pair of transfer gate pulse/reset pulse signal single-wire pins 100T and 100T' are respectively soldered to the pin lands.

The horizontal transfer pulse signal pin land 108S for a signal and the transfer gate pulse/reset pulse signal pin land 108T for a signal are respectively electrically connected with a first relay circuit 66a arranged on the B1-surface. The first relay circuit 66a is electrically connected with first and second horizontal transfer pulse signal connection lands 109S1 and 109S2 for signals, a first transfer gate pulse signal connection land 109T1 for a signal, and a second reset pulse signal connection land 109T2 for a signal.

On the other hand, the horizontal transfer pulse signal pin land 108S' for grounding is electrically connected with first and second horizontal transfer pulse signal connection lands 109S1' and 109S2' for grounding arranged on the B1-surface. Furthermore, the transfer gate pulse/reset pulse signal pin land 108T' for grounding is electrically connected with a first transfer gate pulse signal connection land 109T' for grounding arranged on the B1-surface.

The first horizontal transfer pulse signal line as a coaxial wire extending from the first imaging cable 117C1 is soldered to the pair of first horizontal transfer pulse signal connection lands 109S1 and 109S1' on the B1-surface. The second horizontal transfer pulse signal line of the second imaging cable 117C2 is also similar to this.

Moreover, the first transfer gate pulse signal line as a coaxial wire extending from the first imaging cable 117C1 is electrically connected with the pair of first transfer gate pulse signal connection lands 109T1 and 109T1' on the B1-surface.

Additionally, the second reset pulse signal line as a coaxial wire extending from the second imaging cable 117C2 is electrically connected with the second reset pulse signal connection land 109T2 for a signal and the transfer gate pulse/reset pulse signal pin land 108T' for grounding on the B1-surface.

On the other hand, a pair of vertical transfer pulse signal through holes 106P 106P' are bored from the C1-surface to the C2-surface, and the pair of vertical transfer pulse signal single-wire pins 100P and 100P' are respectively inserted into the through holes from the C1-surface side to the C2-surface side.

On the C2-surface, vertical transfer pulse signal pin lands 108P and 108P' are respectively formed around the vertical transfer pulse signal through holes 106P and 106P', and the vertical transfer pulse signal single-wire pins 100P and 100P' are respectively soldered to the pin lands. The vertical transfer pulse signal pin land 108P for a signal is electrically connected with a second relay circuit 66b on the A1-surface through a connection pattern in the flexible substrate 99 between the C2-surface and the A1-surface (see FIG. 8A). The second relay circuit 66b is electrically connected with first and second vertical transfer pulse signal connection lands 109P1 and 109P2 for signals arranged on the A1-surface through a connection pattern in the A-surface portion.

On the other hand, the vertical transfer pulse signal pin land 108P' for grounding on the C2-surface is electrically connected with first and second vertical transfer pulse signal connection lands 109P1' and 109P2' for grounding arranged on the A1-surface through a connection pattern in the flexible substrate 99 between the C2-surface and the A1-surface.

On the other hand, like the horizontal transfer pulse signal coaxial pin 104S, the image signal coaxial pin 104V is inserted through a image signal through hole 106V piercing the C1-surface to the C2-surface, inserted into a image signal through hole 106V piercing the B2-surface to the B1-surface, and soldered to a pair of image signal pin lands 108V and 108V' formed around the image signal through hole 106V on the B1-surface.

The image signal pin land 108V for a signal is electrically connected with the second relay circuit 66b through a connection pattern in the flexible substrate 99 between the B1-surface and the A1-surface, and the second relay circuit 66b is electrically connected with first and second image signal connection lands 109V1 and 109V2 for signals arranged on the A1-surface.

On the other hand, the image signal pin land 108V for grounding is electrically connected with first and second image signal connection lands 109V1' and 109V2' for grounding arranged on the A1-surface through a connection pattern in the flexible substrate 99 between the B1-surface and the A1-surface.

Additionally, a BA-bending portion 132 is arranged between the B1-surface and the A1-surface, and the A-surface portion is arranged to be substantially vertical to the B-surface portion with the A1-surface facing a central axis of the electrical connector 28 through bending the BA-bending portion 132. Further, the A-surface portion includes first to fourth A-bending portions 134a, 134b, 134c, and 134d arranged side by side in substantially parallel with each other and nearly vertical to the B1-surface.

A relay circuit mounting portion 136 is coupled with the BA-bending portion 132, and the first A-bending portion 134a, a first imaging cable connection land portion 129C1, the second A-bending portion 134b, a first imaging cable connecting portion 128C1, the third A-bending portion 134c, a second imaging cable connection land portion 129C2, the fourth A-bending portion 134d, and a second imaging cable connecting portion 128C2 are sequentially arranged on one lateral side of the relay circuit mounting portion 136.

Further, the second relay circuit 66b is mounted on the relay circuit mounting portion 136. Furthermore, a connection end of the first imaging cable 117C1 is fixed to the first imaging cable connecting portion 128C1 at a position close to the B1-surface, and the first vertical transfer pulse signal line and the first image signal line as coaxial wires extending from the first imaging cable 117C1 are respectively soldered to the first vertical transfer pulse signal connection lands 109P1 and 109P1' and the pair of first image signal connection lands 109V1 and 109V1' arranged in the pair of first imaging cable connection land portions 129C1. The second imaging cable 117C2, the second imaging cable connecting portion 128C2, and the second imaging cable connection land portion 129C2 is also similar to this.

Moreover, the A-surface portion is arranged along the outer periphery of the B-surface portion without overlapping the D-surface portion through bending the first to fourth A-bending portions 134a, 134b, 134c, and 134d.

It is to be noted that the substrate 98 and the C-surface portion of the flexible substrate 99 are positioned by soldering the air supply/water supply signal single-wire pin 100SW1 and others to the air supply/water supply signal pin land 108SW1 and others. Additionally, the C-surface portion and the B-surface portion of the flexible substrate 99 are positioned by soldering the horizontal transfer pulse signal coaxial pin 104S and others to the horizontal transfer pulse signal pin lands 108S and 108S' and others.

Figure 9A:
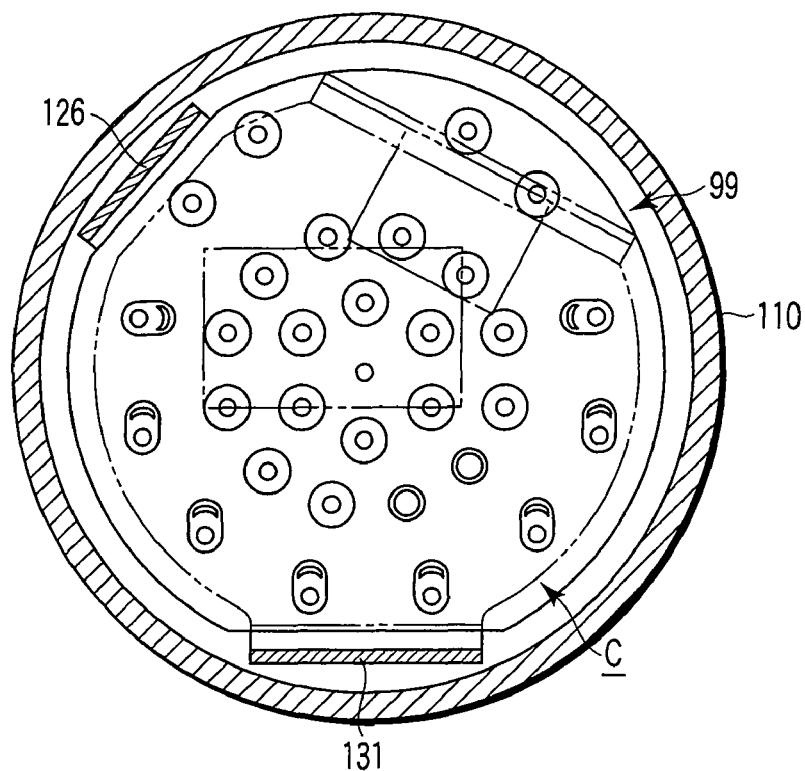
FIG. 9A is a transverse cross-sectional view showing a connector in the endoscope according to the fifth embodiment of the present invention taken along a line IXA-IXA in FIG. 6.
Figure 9B:
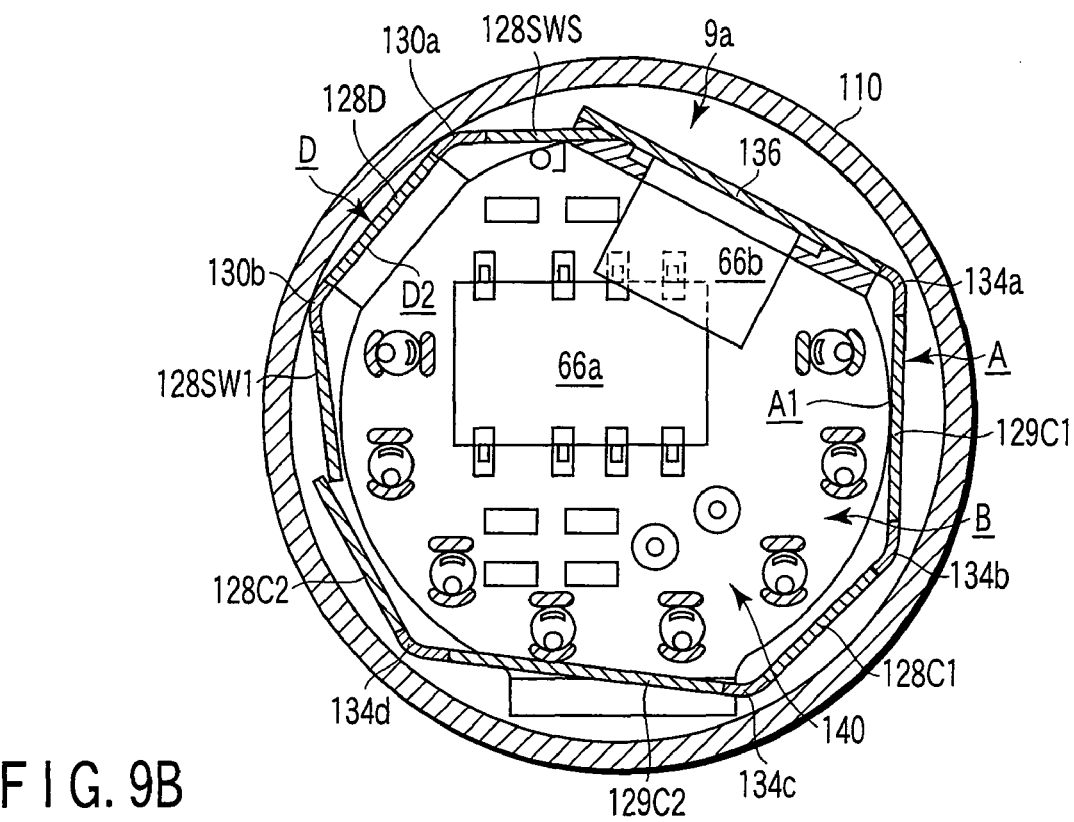
FIG. 9B is a transverse cross-sectional view showing the connector in the endoscope according to the fifth embodiment of the present invention taken along a line IXB-IXB in FIG. 6.

As shown in FIGS. 9A and 9B, the flexible substrate 99 is bent into a cylindrical shape in which a cross-section vertical to an axial direction has a substantially octagonal shape and one end is opened, and the flexible substrate 99 forms an internal space 140. Further, the A1-surface and the D2-surface form an inner peripheral surface, and the connection end of the switching cable 117SW2 and others and the first and second relay circuits 66a and 66b mounted on the flexible substrate 99 are accommodated in the internal space 140. Furthermore, the flexible substrate 99 bent into the cylindrical shape is accommodated in the shield tube 110 coaxially with the shield tube 110.

Figure 10:
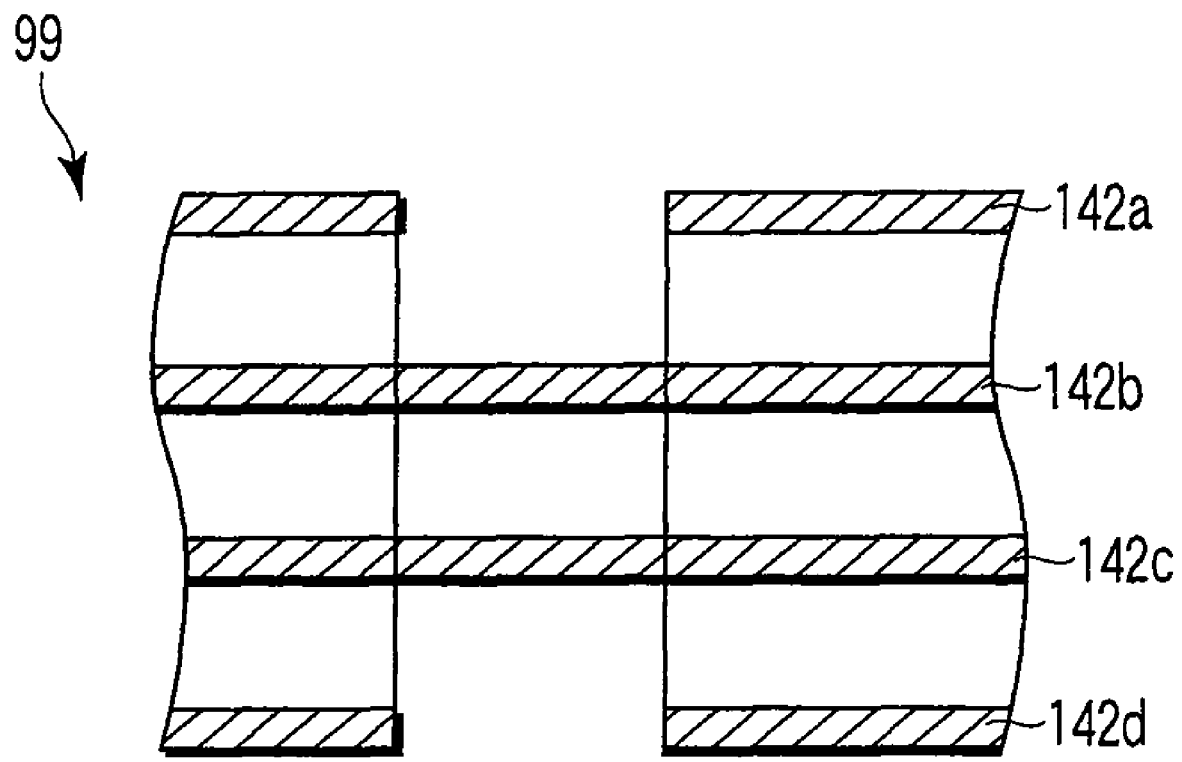
FIG. 10 is a longitudinal cross-sectional view showing the flexible substrate in the endoscope according to the fifth embodiment of the present invention.

Moreover, as shown in FIG. 10, the flexible substrate 99 includes a multilayer structure wherein a first layer 142a and a fourth layer 142d sandwich second and third layers 142b and 142c therebetween. A signal connection pattern and a grounding connection pattern are respectively patterned in the second and third layers 142b and 142c. Additionally, the first layer 142a and the fourth layer 142d serve as grounding layers. It is to be noted that the first and fourth layers 142a and 142d are not formed in the-bending portions.

A function of the endoscope system 14 according to the embodiment will now be explained. In the normal optical observation mode, a first information signal ΦD1 is transmitted from the first CCD information storage portion 68a to the driving circuit 70 in the processor 46 through the information relay circuit 64, the information signal line, the information signal connection land 109D on the D2-surface of the flexible substrate 99, the connection pattern between the D2-surface and the C2-surface, the information signal pin land 108D on the C2-surface, and the information signal single-wire pin 100D.

Thereafter, a first vertical transfer pulse signal ΦP1 is transmitted from the driving circuit 70 to the first image pick up unit 24a through the vertical transfer pulse signal single-wire pin 100P, the vertical transfer pulse signal pin land 108P on the C2-surface, the connection pattern between the C2-surface and the A1-surface, the second relay circuit 66b on the A1-surface, the connection pattern of the A-surface portion, the first vertical transfer pulse signal connection land 109P1 on the A1-surface, and the first vertical transfer pulse signal line.

Further, a first horizontal transfer pulse signal ΦS1 is transmitted from the driving circuit 70 to the first image pick up unit 24a through the horizontal transfer pulse signal coaxial pin 104S, the horizontal transfer pulse signal pin land 108S on the B1-surface, the connection pattern of the B-surface portion, the first relay circuit 66a of the B1-surface, the connection pattern of the B-surface portion, the first horizontal transfer pulse signal connection land 109S1 on the B1-surface, and the first horizontal transfer pulse signal line.

Furthermore, a first transfer gate pulse signal ΦT1 is transmitted from the driving circuit 70 to the first image pick up unit 24a through the transfer gate pulse/reset pulse signal single-wire pin 100T, the transfer gate pulse/reset pulse signal pin land 108T on the B1-surface, the connection pattern of the B-surface portion, the first relay circuit 66a on the B1-surface, the connection pattern of the B-surface portion, the first transfer gate pulse signal connection land 109T1 on the B1-surface, and the first transfer gate pulse signal line. Therefore, the first image pick up unit 24a is driven.

Then, a first image signal Vout1 is transmitted from the first image pick up unit 24a to the image processing circuit 72 in the processor 46 through the first image signal line, the first image signal connection land 109V1 on the A1-surface, the connection pattern of the A-surface portion, the second relay circuit 66b on the A1-surface, the connection pattern between the A1-surface and the B1-surface, the image signal pin land 108V on the B1-surface, and the image signal coaxial pin 104V, thereby displaying a normal optical observation image on the monitor 74.

In the fluorescent observation mode, a second information signal ΦD2 is transmitted from the second CCD information storage portion 68a to the driving circuit 70 in the processor 46 like the first information signal ΦD1 in the normal optical observation mode.

Then, a second vertical transfer pulse signal ΦP2 is transmitted from the driving circuit 70 to the second image pick up unit 24b through the second relay circuit 66b on the A1-surface, the connection pattern of the A-surface portion, the second vertical transfer pulse signal connection land 109P2 on the A1-surface, and the second vertical transfer pulse signal line.

Further, a second horizontal transfer pulse signal ΦS2 is transmitted from the driving circuit 70 to the second image pick up unit 24b through the second relay circuit 66a on the B1-surface, the connection pattern of the B-surface portion, the second horizontal transfer pulse signal connection land 109S2 on the B1-surface, and the second horizontal transfer pulse signal line. Furthermore, a second reset pulse signal ΦRS2 is transmitted from the driving circuit 70 to the second image pick up unit 24b through the first relay circuit 66a on the B1-surface, the connection pattern of the B-surface portion, the second reset pulse signal connection land 109T2 on the B1-surface, and the second reset pulse signal line. Therefore, the second image pick up unit 24b is driven.

Then, a second image signal Vout2 is transmitted from the second image pick up unit 24b to the image processing circuit 72 in the processor 46 through the second image signal line, the second image signal connection land 109V2 on the A1-surface, the connection pattern of the A-surface portion, and the second relay circuit 66b on the A1-surface, thereby displaying a fluorescent observation image on the monitor 74.

Therefore, the endoscope system 14 according to the embodiment includes the following effect. Since the switching circuit portion 26 is arranged in the electrical connector 28, the operating portion 27 and others that are held by an operator to be operated can be reduced in size as compared with an example where the switching circuit portion 26 is arranged in the operating portion 27 and others. Therefore, the operability of the endoscope 16 is improved.

Furthermore, since the switching circuit portion 26 is directly connected with the electrical connector 28, a structure connecting the switching circuit portion 26 and the electrical connector 28 does not have to be, thereby simplifying the part structure. Accordingly, the structure of the endoscope 16 is further simplified.

Moreover, the flexible substrate 99 forming the switching circuit portion 26 is bent into the cylindrical shape to form the internal space 146, and the connection end of the switching cable 117SW2 and others, and the first and second relay circuits 66a and 66b mounted on the flexible substrate 99 are accommodated in the internal space 140. The switching circuit portion 26 has a compact structure in the manner, and the entire connector portion 49 can have a compact structure.

Additionally, in the first and second imaging cable connecting portions 128C1 and 128C2 on the A1-surface, the connection ends of the first and second imaging cables 117C1 and 117C2 are fixed to positions close to the B1-surface. That is, connecting positions of the connection ends of the first and second imaging cables 117C1 and 117C2 are positions sufficiently apart from the inserting position of the transmission cable 114 with respect to the shield tube 110. Therefore, in connection to the flexible substrate 99, the first and second imaging cables 117C1 and 117C2 are prevented from being sharply bent, thereby improving resistance properties.

Further, the D-surface portion is arranged along the outer periphery of the C-surface portion through bending the first and second D-bending portions 130a and 130b of the D-surface portion. Here, in the case where the first and second D-bending portions 130a and 130b are not provided and the D-surface portion is bent to form a circumferential wall of the cylinder along the C-surface portion, a bending stress is applied to the air supply/water supply signal connection land 109SW1 and others, thus deteriorating the resistance properties of the soldered portion. In the embodiment, the air supply/water supply cable connecting portion 128SW1 and others have a flat shape, and the bending stress is not applied to the air supply/water supply signal connection land 109SW1 and others, thereby improving the resistance properties. The A-surface portion also includes the same effect.

Furthermore, the air supply/water supply signal line and others as the single electric wire is soldered to the D2-surface. On the other hand, the vertical transfer pulse signal line and others as the coaxial electric wire is soldered to the A1-surface. That is, the same type of electric wire is soldered to the same surface, which improves the workability in soldering.

Here, in an endoscope like that in Jpn. Pat. Appln. KOKAI Publication No. 6-154155 described in Background Art, various kinds of signals are transmitted/received between the image pick up unit and the video processor. Various kinds of electrical devices are used as well as the endoscope in a medical scene, and hence noise may occur in a signal due to an influence of an external electromagnetic field at, e.g., the connecting portion between a signal line extending from the image pick up unit and the connector in some cases.

Moreover, signals transmitted/received between the image pick up unit and the video processor include, e.g., a high-frequency signal such as a driving signal to drive the image pick up unit as well as a low-frequency signal such as a image signal to display an image on the monitor. Therefore, noise may occur in the low-frequency signal due to an influence of the high-frequency signal at, e.g., the connecting portion between the signal line and the connector in some cases.

In the embodiment, the first relay circuit 66a switches the horizontal transfer pulse signal ΦS and the transfer gate pulse signal ΦT as high-frequency signals, and the second relay circuit 66b switches the vertical transfer pulse signal ΦP and the image signal Vout as low-frequency signals. That is, the switching for the low-frequency signals and the high-frequency signals is performed respectively by the different relay circuits 66a and 66b. Therefore, the high-frequency signal and the low-frequency signal can be prevented from interfering with each other in the relay circuits 66a and 66b.

Additionally, the horizontal transfer pulse signals ΦS1 and ΦS2 as high-frequency signals are transmitted through the connection pattern formed in the B-surface portion among the horizontal transfer pulse signal coaxial pin 104S electrically connected with the horizontal transfer pulse signal pin lands 108S and 108S' on the B1-surface, the horizontal transfer pulse signal pin lands 108S and 108S' on the B1-surface, the first relay circuit 66a on the B1-surface, and the horizontal transfer pulse signal connection lands 109S1, 109S1', 109S2, and 109S2 on the B1-surface. Here, in the case where the horizontal transfer pulse signals ΦS1 and ΦS2 are transmitted on, e.g., the C-surface portion of the flexible substrate 99, noise occurs in other low-frequency signals due to the horizontal transfer pulse signals ΦS1 and ΦS2 as high-frequency signals. In the embodiment, the horizontal transfer pulse signals ΦS1 and ΦS2 are transferred on the B-surface portion alone in the flexible substrate 99, thereby avoiding interference with other low-frequency signals. Further, the transfer gate pulse signals ΦT1 and ΦT2 as high-frequency signals are also transferred on the B-surface portion alone, thus avoiding interference with other low-frequency signals.

Furthermore, in the flexible substrate 99, the first layer 142a and the fourth layer 142d as the grounding layers sandwich the second and third layers 142b and 142c wherein the signal connection pattern and the grounding connection pattern are respectively patterned. Therefore, electric field intensity in the connection pattern of the second layer 142b is improved.

Moreover, the flexible substrate 99 including the grounding layers is bent into the cylindrical shape to form the internal space 140, and the connection ends of the switching cable 117SW2 and others and the first and second relay circuits 66a and 66b mounted on the flexible substrate 99 are accommodated in the internal space 140. Thus, the flexible substrate 99 electrically shields the internal space 140, thereby preventing an external electric field from interfering with various kinds of signals.

As explained above, in the embodiment, mutual interference of a plurality of types of signals in the flexible substrate 99 is avoided, electric field intensity in each connection pattern in the flexible substrate 99 is improved, and an external electric field is prevented from interfering with various kinds of signals in the switching circuit portion 26. In this manner, in the switching circuit portion, a shield to avoid occurrence of noise in signals transmitted/received between the endoscope 16 and the processor 49 is formed, thereby improving a transmission quality.

FIGS. 11 and 12 show a sixth embodiment according to the present invention. Like reference numerals denote structures having the same functions as those in the first embodiment, thereby omitting an explanation thereof. In the embodiment, in order to transmit a horizontal transfer pulse signal as a high-frequency signal, a horizontal transfer pulse signal line as a coaxial electric wire is directly connected with a horizontal transfer pulse signal coaxial pin.

As shown in FIG. 11, in an endoscope system 14 according to the embodiment, the first and second CCD information storage portions 68a and 68b and the information relay circuit 64 depicted in FIG. 3 are not provided, and a changeover switch 42 outputs a switching signal ΦSW2 to a driving circuit 70 in a processor 46 in place of the information relay circuit 64. The driving circuit 70 that has received the switching signal ΦSW2 switches a first driving circuit 70a to drive a first image pick up unit 24a and a second driving circuit 70b to drive a second image picks up unit 24b so that one of the driving circuits 70a and 70b is activated.

Furthermore, a first horizontal transfer pulse signal ΦS1 is output from the first driving circuit 70a to the first image pick up unit 24a without passing a first relay circuit 66a. Likewise, a second horizontal transfer pulse signal ΦS2 is output from the second driving circuit 70b to the second image pick up unit 24b without passing a second relay circuit 66b.

FIG. 12 shows a first horizontal transfer signal coaxial pin 104S1 (which will be simply referred to as a coaxial pin 104S1 hereinafter) according to the embodiment. The coaxial pin 104S1 includes an inner conductor 144 having an elongated cylindrical shape, and an outer conductor having an elongated cylindrical shape is fitted on the outside of the inner conductor 144. An insulation member 148 is interposed between the inner conductor 144 and the outer conductor 146 on a distal end side of the coaxial pin 104S1, and the insulation member 148 positions the inner conductor 144 and the outer conductor 146 in such a manner that they do not come into contact with each other. Moreover, the inner conductor 144, the outer conductor 146, and the insulation member 148 are fastened and fixed by using an annular support member 150, thereby maintaining a positional relationship among the inner conductor 144, the outer conductor 146, and the insulation member 148.

The coaxial pin 104S1 is inserted into the through hole 106 formed in the substrate 98. Additionally, the inner conductor 144 of the coaxial pin 104S1 is inserted into the first horizontal transfer pulse signal through holes 106S1 formed in the C-surface portion and the B-surface portion of the flexible substrate 99 in alignment with each other, and protrudes from the C-surface portion. Further, a bead core 152 to avoid EMC is fitted on the outside of the inner conductor 144 between the C-surface portion and the B-surface portion. An outer face of the bead core 152 is in contact with the C2-surface, and an inner face of the same is in contact with the B2-surface.

On the other hand, the outer conductor 146 of the coaxial pin 104S1 is soldered to the substrate 98 in the through hole 106 in the substrate 98. Furthermore, an inner end of the outer conductor 146 has a structure wherein a protruding portion 154 extends from a part of an annular inner end face. The annular inner face of the outer conductor 146 is arranged at a position close to the C1-surface of the flexible substrate 99, and the protruding portion 154 of the outer conductor 146 is inserted into the first horizontal transfer pulse signal through holes 106S1 formed in the C-surface portion and the B-surface portion and protrudes from the C-surface portion. It is to be noted that the protruding portion 154 of the outer conductor 146 is in contact with an outer peripheral surface of the bead core 152 between the C-surface portion and the B-surface portion.

A first horizontal transfer pulse signal line 156 as a coaxial electric wire is connected with the coaxial pin 104S1 in the internal space 140 of the flexible substrate 99. That is, a horizontal transfer pulse signal line 156a for a signal is soldered to the inner conductor 144 of the coaxial pin 104S1, and a horizontal transfer pulse signal line 156b for grounding is soldered to the outer conductor 146 of the coaxial pin 104S1.

Moreover, a second horizontal transfer pulse signal coaxial pin has the same structure as the first horizontal transfer pulse signal coaxial pin 104S1, and the second horizontal transfer pulse signal line is directly connected with the second horizontal transfer pulse signal coaxial pin like the first horizontal transfer pulse signal line 156.

A function of the endoscope system 14 according to the embodiment will now be explained. In the normal optical observation mode, various kinds of signals are transmitted from the first driving circuit 70a to the first image pick up unit 24a. Of the signals, the first horizontal transfer pulse signal ΦS1 is directly transmitted from the first horizontal transfer pulse signal coaxial pin 104S1 to the first horizontal transfer pulse signal line 156.

In case of performing fluorescent observation, the changeover switch 42 is operated. When the changeover switch 42 is operated, the second driving circuit 70b is actuated in place of the first driving circuit 70a. In the fluorescent observation mode, various kinds of signals are transmitted from the second driving circuit 70b to the second image pick up unit 24b. Like the first horizontal transfer pulse signal ΦS1, the second horizontal transfer pulse signal ΦS2 is directly transmitted from the second horizontal transfer pulse signal coaxial pin to the second horizontal transfer pulse signal line.

Therefore, the endoscope system 14 according to the embodiment includes the following effect. In the embodiment, the first and second horizontal transfer pulse signals ΦS1 and ΦS2 each having a high frequency are directly transmitted to the first and second horizontal transfer pulse signal lines from the first and second horizontal transfer pulse signal coaxial pins 104S1 without passing a connection pattern in the flexible substrate 99. In the case where the high-frequency signal is transmitted through the connection pattern in the flexible substrate 99, noise may possibly occur in a low-frequency signal transmitted through another connection pattern in the flexible substrate, but occurrence of the noise is avoided in the embodiment.

Moreover, the bead core 152 to avoid EMC is arranged between the C-surface portion and the B-surface portion with the outer face of the bead core 152 being in contact with the C2-surface and the inner face of the same being in contact with the B2-surface. Therefore, the bead core 152 can be readily fixed when assembling the bead core 152.

In the embodiment, an insulation member having the same shape as the bead core 152 may be arranged in place of the bead core 152. In the case, the protruding portion 154 can be prevented from being deformed to come into contact with the inner conductor 144.

In the foregoing embodiments, the image pick up unit for normal optical observation and the image pick up unit for fluorescent observation are used as the first and second image pick up units. However, various image pick up units can be used as the first image pick up unit and the second image pick up unit. For example, the image pick up unit for normal optical observation, the image pick up unit for fluorescent observation, and an image pick up unit for enlarging observation can be arbitrarily combined and used.

INDUSTRIAL APPLICABILITY

The present invention provides an endoscope to perform observation using the plurality of image pick up units, which has a simplified structure and a reduced cost, and an endoscope system including such an endoscope.

The invention claimed is:

1. A switching circuit member for an endoscope, wherein the switching circuit member is configured to be coupled with a connector to be connected with an external device that performs signal processing, is configured to be electrically connected with each of a plurality of image pick up units to pick up an observation image, and is configured to switch the plurality of image pick up units so that one of the image pick up units transmits/receives at least one type of signal to/from the connector, characterized in that the switching circuit member includes a shield configured to avoid occurrence of noise in the signal transmitted/received between the plurality of image pick up units and the external device, each image pick up unit transmits/receives a plurality of types of signals to/from the external device, and the shield is configured to avoid mutual interference between the plurality of types of signals in the switching circuit member, wherein the plurality of types of signals include a high-frequency signal and a low-frequency signal, the switching circuit member further includes a flexible substrate including a plurality of surface portions wherein a signal line to electrically connect each image pick up unit with the switching circuit member and a connection pin to electrically connect the external device with the switching circuit member are configured to be connected to the plurality of surface portions, the plurality of surface portions include one surface portion wherein the signal line to transmit the high-frequency signal and the connection pin to transmit the high-frequency signal are configured to be connected to the one surface portion and a connection pattern provided in the one surface portion serves to transmit the high-frequency signal, and the plurality of surface portions include one surface portion wherein the signal line to transmit the low-frequency signal and the connection pin to transmit the low-frequency signal are configured to be connected to the one surface portion and a connection pattern provided in the one surface portion serves to transmit the low-frequency signal, and wherein one surface portion of the high-frequency signal is different from one surface portion of the low-frequency signal.

2. The switching circuit member for the endoscope according to claim 1, characterized in that the switching circuit member includes a first relay circuit to switch the high-frequency signal and a second relay circuit to switch the low-frequency signal.

3. The switching circuit member for the endoscope according to claim 1, characterized in that the flexible substrate includes at least one inner layer including a connection pattern to transmit the signal and a pair of outer layers for grounding sandwiching the inner layer.

4. The switching circuit member for the endoscope according to claim 1, characterized in that the flexible substrate is bent to form an internal space, and the flexible substrate includes: a signal line connecting portion, to be connected to a connection end of the signal line to electrically connect each image pick up unit with the switching circuit member and provided to the flexible substrate such that the connection end of the signal line is arranged in the internal space; and an electronic part provided to the flexible substrate so as to be arranged in the internal space and to perform the switching.

5. An endoscope comprising the switching circuit member, according to claim 1.

* * * * *